United States Patent [19]
Watanabe et al.

[11] Patent Number: 5,909,099
[45] Date of Patent: Jun. 1, 1999

[54] ELECTRIC VEHICLE CHARGING SYSTEM INCLUDING REFRIGERANT SYSTEM

[75] Inventors: Kunihiko Watanabe; Heiji Kuki, both of Yokkaichi; Shuji Arisaka; Toshiro Shimada, both of Osaka, all of Japan

[73] Assignees: Sumitomo Wiring Systems, Ltd., Yokkaichi; Sumitomo Electric Industries, Ltd., Osaka, both of Japan

[21] Appl. No.: 08/907,000

[22] Filed: Aug. 6, 1997

[30] Foreign Application Priority Data

| Aug. 7, 1996 | [JP] | Japan | 8-208601 |
| Feb. 26, 1997 | [JP] | Japan | 9-042313 |
| Mar. 5, 1997 | [JP] | Japan | 9-049982 |
| Mar. 21, 1997 | [JP] | Japan | 9-068073 |
| Jun. 26, 1997 | [JP] | Japan | 9-170703 |

[51] Int. Cl.$^6$ ............................................. H01M 10/46
[52] U.S. Cl. ................................................ 320/108
[58] Field of Search .......................... 320/103, 104, 320/108, 109, FOR 101, DIG. 33, DIG. 34; 336/DIG. 2

[56] References Cited

U.S. PATENT DOCUMENTS

| 4,543,552 | 9/1985 | Fantou . | |
| 5,216,402 | 6/1993 | Carosa . | |
| 5,408,209 | 4/1995 | Tanzer et al. . | |
| 5,412,304 | 5/1995 | Abbott . | |
| 5,461,215 | 10/1995 | Haldeman . | |
| 5,545,966 | 8/1996 | Ramos et al. | 320/108 |
| 5,594,315 | 1/1997 | Ramos et al. | 320/108 |
| 5,684,380 | 11/1997 | Woody et al. | 320/108 |

FOREIGN PATENT DOCUMENTS

| 0-638-912-A2 | 2/1995 | European Pat. Off. . |
| 0-651-404-A1 | 5/1995 | European Pat. Off. . |
| 0-680-055-A1 | 11/1995 | European Pat. Off. . |
| 0-680-058-A2 | 11/1995 | European Pat. Off. . |
| 0-680-059-A2 | 11/1995 | European Pat. Off. . |
| 43-08-974-A1 | 9/1994 | Germany . |
| A-5-258962 | 10/1993 | Japan . |
| A-5-260671 | 10/1993 | Japan . |
| A-6-14470 | 1/1994 | Japan . |

*Primary Examiner*—Edward H. Tso
*Attorney, Agent, or Firm*—Oliff & Berridge, PLC

[57] ABSTRACT

A charging system for use with an electric vehicle in that a primary coil 32 is structured in such a manner that a conductive pipe 34 is wound around a primary core 33. Cooling water is allowed to circulate through the conductive pipe 34, while the cooling water is cooled by a radiator device provided on the charging unit side. To the two ends of the conductive pipe 34, there are connected the core wires of a charging power cable 40 through energizing terminals 37, so that the primary coil 32 can be excited.

26 Claims, 28 Drawing Sheets

ELECTRIC VEHICLE CHARGING SYSTEM INCLUDING REFRIGERANT SYSTEM

BACKGROUND OF THE INVENTION

The present invention relates to a charging system for charging an electric vehicle by use of electromagnetic induction and, in particular, to an improved coil cooling structure.

A charging system of this type is able to supply power to an electric vehicle with no intervention of an electric contact, that is, in a non-contact manner. Due to this, the charging system of this type provides various advantages and there have been proposed various structures for such charging system. Referring to the basic structure of the charging system, for example, as disclosed in Unexamined Japanese Patent Publication 5-258962, 5-260671, 6-14470 and the like, there is applied the principle of a transformer that coils are respectively wound around primary and secondary cores and, when charging the electric vehicle, an alternating current is allowed to flow through the primary coil to thereby cause the secondary coil to generate an electromotive force due to electromagnetic coupling.

The charging system of this type is strongly required to be compact as a whole and, in order to attain such compact charging system, it is necessary to cool the coils sufficiently during the charging operation of the electric vehicle. As described above, the basic principle of the present charging system is derived from the transformer and thus, as the cooling structure of the charging system, there is applied a similar structure to the transformer; for example, in U.S. Pat. No. 5,412,304, as shown in FIGS. 31 and 32, there is employed a structure in which a core 2 is stored in a housing 1, a primary coil 3 is wound around the outer periphery of the core 2, and there are formed a large number of cool air passages 4 extending along the primary coil 3 as well as air exhaust ports 5 in communication with the cool air passage 4. And, a cool air supply hose 6 coming from a cooling device is connected to the housing 1 so that the open air can be supplied into the cool air passages 4, that is, if the open air flows through the cool air passages 4 and flows out from the air exhaust ports 5, then the heat of a primary coil unit as well as the heat of a secondary coil unit disposed adjacent to the primary coil unit can be discharged.

However, in the above-mentioned structure, the heat generated in the primary coil 3 is cooled only from the outside thereof and thus the cooling efficiency of the primary coil 3 cannot be enhanced to a sufficient degree, so that the heat is easy to remain in the interior portion of the primary coil 3. Also, since heat is generated not only in the primary coil 3 but also in the core 2, in order to cool the heat of the core 2, as shown in FIG. 32, it is necessary to provide a refrigerant passage 4 in the neighborhood of the core 2. Further, for the sake of efficient cooling of the primary coil 3, there are arranged a large number of refrigerant passages 4 extending along the primary coil 3, which is unable to enhance the rate of occupation of the primary coil 3 but increases the size of the whole charging system.

Also, in the above-mentioned structure, there is found a further problem: that is, because the open air is simply supplied to the neighborhood of the heat generated portions of the structure, the cooling efficiency is still not sufficiently high and the heat is easy to remain in the interior portion of a charging coupler.

Further, in the above-mentioned structure, there is found a still further problem: that is, in order to remove the heat within the coil unit, it is necessary to provide a special cooling device.

SUMMARY OF THE INVENTION

The present invention aims at eliminating the drawbacks found in the above-mentioned conventional charging systems. Accordingly, it is an object of the invention to provide a charging system for charging an electric vehicle, in which a primary coil unit or a secondary coil unit can be cooled with no need for provision of a special cooling device, thereby being able to provide a compact charging system or a large-capacity charging system.

In the charging system of this type, in order to make a magnetic circuit compact, an alternating current for a primary coil is changed into a high-frequency current. As a result of this, there is generated a skin effect that the current flowing through the primary coil is localized on the outer peripheral side of the section of the primary coil, so that the central portion of the section of the primary coil can scarcely function as the current passage. The present invention is made in the light of such circumstances.

A charging system according to the invention is characterized in that a primary coil or a secondary coil is composed of a conductive pipe and a refrigerant is allowed to flow through the conductive pipe to thereby cool the primary or secondary coil.

According to the present structure, since the coil is formed of a conductive pipe and the refrigerant is allowed to flow through the interior portion of the coil, the coil conductor itself, which is a source of generation of Joule heat, can be cooled from the inside thereof, so that the coil can be cooled with high efficiency. Also, due to the fact that the coil is formed of a conductive pipe, even if there occurs a skin effect when a high-frequency current is allowed to flow through the coil, there is no possibility that the conductor resistance can increase to thereby lower the cooling efficiency of the coil.

Also, a charging system according to the invention is characterized in that a primary coil or a secondary coil is composed of a conductive pipe and also in that the conductive pipe is wound around a core in a heat-transferable manner and a refrigerant is allowed to flow through the interior portion of the conductive pipe to thereby cool the coil and core.

According to the present structure, since even heat generated in the core due to an eddy-current loss is transferred to the conductive pipe and is then transferred to the refrigerant flowing through the conductive pipe, an increase in the temperatures of not only the coil but also the core can be restricted effectively.

Further, a charging system according to the invention is characterized by a high-frequency power supply device for charging; a housing which can be set in a receive portion provided in a secondary coil arranging portion of an electric vehicle; a primary side core which, when it is stored within the housing and is then set in the receive portion of the electric vehicle, can be coupled to the secondary side core of a secondary coil to thereby form a magnetic circuit; a primary coil formed of a conductive pipe and wound around the primary side core in a heat-transferable manner; a power cable for charging interposed between the high-frequency power supply device and housing to apply a high-frequency current from the high-frequency power supply device to the primary coil; a refrigerant supply pipe which is so disposed as to extend along the charging power cable and is used to supply a refrigerant to the interior portion of the conductive pipe; a radiator device which is so provided as to be connected with the refrigerant supply pipe and is used to radiate the heat of the refrigerant heated because it has cooled the primary coil and primary side core; and, a circulation pump which can be operated in combination with a charging operation and is used to return the refrigerant, which is heat-radiated and thus cooled in the radiator device, to the primary coil side through the refrigerant supply pipe to thereby circulate the refrigerant.

According to the present structure, to achieve a charging operation, the housing incorporating the primary coil therein is set in the receive portion of the electric vehicle and the high-frequency power source for charging is then allowed to apply a high-frequency current to the primary coil through the charging power cable. Also, the circulation pump is operated in combination with this charging operation, so that the refrigerant is supplied to the primary coil side through the refrigerant supply pipe arranged along the charging power cable and is allowed to circulate through the radiator device.

During the charging operation, the high-frequency current flowing through the primary coil causes the conductive pipe forming the primary coil to generate Joule heat therein. The thus generated Joule heat is transferred to the refrigerant flowing through the interior portion of the conductive pipe, and the refrigerant heated by such Joule heat is then carried out to the outside. After then, the refrigerant is delivered through the refrigerant supply pipe to the radiator device, in which the refrigerant is radiated and is thus cooled. Also, on the primary side core as well, there is generated heat. The heat generated on the core side is transferred to the conductive pipe because the conductive pipe is wound around the primary side core, while the thus heated conductive pipe is cooled together with the primary coil by the refrigerant passing through the conductive pipe.

And, the refrigerant, which is heated by cooling the primary coil and core, is allowed to flow through the refrigerant supply pipe and arrive at the radiator device, in which the refrigerant is cooled and returned again to the primary coil side for circulation.

Therefore, according to the present structure as well, the coil conductor itself, which is a source of generation of Joule heat, is cooled from the inside thereof. That is, the present structure can realize efficient cooling and thus can contribute toward making compact the whole of the charging system. Further, since the primary coil is formed of the conductive pipe, even if there occurs a skin effect when the high-frequency current is applied to the primary coil, there is no possibility that the conductor resistance can increase, which prevents not only the lowered efficiency but also the excessive heat generation.

According to the invention, there is provided a charging system in which the primary coil is wound around the primary side core in two or more layers which are superimposed on top of each other, and the refrigerant is allowed to flow from the inner peripheral side of the primary coil toward the outer peripheral side thereof.

In the present structure, since the refrigerant flows from the inner peripheral side of the primary coil, that is, from the neighborhood of the primary side core toward the outer peripheral side of the primary coil, the refrigerant near to the primary side core is decreased in temperature, so that the primary side core can be cooled with high efficiency.

According to the invention, there is provided a charging system in which there is formed a projecting portion or a recessed portion in the inner surface of the conductive pipe.

Use of this structure increases a contact area between the conductive pipe and the refrigerant flowing through the conductive pipe as well as causes a turbulent flow in the flow of the refrigerant to thereby enhance the efficiency of heat exchange between them, with the result that the cooling efficiency of the charging system can be improved.

According to the invention, there is provided a charging system in which a secondary coil disposed on the electric car side is also formed of a conductive pipe and a refrigerant on the primary side is made to flow through the interior portion of the present conductive pipe to thereby cool the secondary coil.

In the present structure, because the secondary coil side can be cooled by use of a cooling system provided on the primary coil side, not only the structure of the charging system on the electric car side can be simplified and reduced in weight, but also the freedom of design thereof can be enhanced.

According to the invention, there is provided a charging system in which an insulation layer is formed in the inner surface of the conductive pipe and a water-system refrigerant is used as a refrigerant.

In the present structure, since the insulation layer is formed in the inner surface of the conductive pipe, it is possible to use a water-system refrigerant which is inexpensive and easy to handle.

According to the invention, there is provided a charging system in which a plurality of refrigerant discharge holes are formed in the peripheral surface of the conductive pipe in such a manner that they respectively extend through the conductive pipe peripheral surface.

In the present structure, the refrigerant can be poured from the refrigerant discharge holes directly to the respective parts of the structure such as the core and the like, so that the respective parts of the structure can be cooled with high efficiency.

According to the invention, there is provided a charging system in which, between the primary side or secondary side core and coil, there is formed a passage space which is used to flow the refrigerant discharged from the refrigerant discharge holes.

In the present structure, due to provision of the passage space between the coil and core, the refrigerant is made easy to flow, which prevents the refrigerant against stagnation, thereby being able to enhance the cooling efficiency of the charging system.

Now, according to one aspect of the invention there is provided a charging system for use in an electric car in which a charging coupler is mounted into a receive portion provided in an electric car, a primary coil is excited by a charging power source to thereby cause a secondary coil on the electric car receive portion side to generate an electromotive force therein, and the battery device of the electric car is charged by the thus generated electromotive force, characterized in that there are provided a refrigerant circulation passage for circulating a refrigerant through the charging coupler, and radiating means for discharging heat from the refrigerant flowing through the refrigerant circulation passage, and the charging coupler is cooled by means of circulation of the refrigerant.

According to the invention, the refrigerant flows within the interior portion of the charging coupler through the refrigerant circulation passage, and the heat generated in the charging coupler is removed externally of the connector by the refrigerant. And, such heat is radiated by the radiator means and the thus cooled refrigerant flows again through the refrigerant circulation passage so as to cool the charging coupler.

Also, according to the invention, since the cool refrigerant flows repeatedly within the interior portion of the charging coupler, the heat generated in the charging coupler can be removed with high efficiency. And, because the refrigerant circulates through the refrigerant circulation passage, the refrigerant can be used with no waste. Further, not only the air but also a gas refrigerant or a liquid refrigerant having an excellent cooling capability can be used, which is further convenient for enhancement in the cooling efficiency.

The invention is characterized in that the refrigerant circulation tube forming a portion of the refrigerant circulation passage is integrally united with the power cable which is used to supply power to the charging coupler.

According to this structure, since the refrigerant circulation tube used to flow the refrigerant therethrough is formed integral with the power cable, the present charging system is easy to handle when charging the electric vehicle.

The invention is characterized in that it uses as radiating means a radiator device which is incorporated integrally in the power source device.

According to this structure, because the radiator device is incorporated integrally in the charging power device, the whole charging system can be made compact.

The invention is characterized in that the primary coil of the charging coupler is formed of a conductive pipe and the present conductive pipe is used as a portion of the refrigerant circulation passage through which the refrigerant is allowed to flow.

According to this structure, since the primary coil is formed of the conductive pipe, the coil itself can be used as a portion of the refrigerant circulation passage. As a result of this, not only the whole charging system can be made compact but also a cooling operation can be executed in the neighborhood of a source of generation of heat, which leads to an excellent cooling efficiency.

Now, according to the invention, there is provided a charging system in which a primary coil unit provided in a charging coupler is excited by a power source for charging to thereby generate an electromotive force in a secondary unit which is provided on the electric vehicle side, and the battery device of the electric vehicle is charged by the thus generated electromotive force, characterized in that the primary and secondary coil units respectively include primary and secondary refrigerant passages for cooling the primary and secondary coil units, and there are provided passage joints respectively for connecting the refrigerant passages of the primary and secondary coil units with each other.

According to the present structure, since the refrigerant passages of the primary and secondary coil units are connected with each other by the passage joints, a device for supplying the refrigerant may be provided only one of the electric vehicle side and charging power source side. Thanks to this, not only the structure of the other side can be simplified and reduced in weight but also the freedom of design of the charging system can be enhanced.

The present invention is also characterized in that the passage joints are disposed opposed not only to the charging coupler but also to the receive portion provided in the electric vehicle for receiving the charging coupler, and the passage joints are connected with each other when the charging coupler is mounted into the receive portion of the electric vehicle, thereby bringing the primary side and secondary side refrigerant passages into communication with each other.

According to the invention, since the passage joints are arranged opposed to each other, they can be connected with each other in accordance with an operation to set the charging coupler in the electric car side receive portion, that is, the connecting operation of the passage joints is easy to perform.

The invention is characterized in that the passage joints each includes a valve mechanism for closing its associated refrigerant passage when the passage joints are not connected with each other.

In the present structure, when the passage joints are not connected with each other, the valve mechanisms thereof are closed to prevent the refrigerant from passing through the passage joints. This prevents the refrigerant from leaking externally of the refrigerant passages.

The invention is also characterized in that the primary and secondary coils are respectively formed of conductive pipes and the primary side and secondary side refrigerant passages are respectively formed by the present conductive pipes.

According to the present structure, since the coils are formed of the conductive pipes, the coils themselves can be used as part of the refrigerant passages. As a result of this, not only the whole charging system can be made compact but also cooling can be achieved in the neighborhood of a source of heat generation, which leads to an excellent cooling efficiency.

Further, the invention pays attention to the fact that an electric vehicle inherently includes a cooling device for cooling various electrical equipment such as an inverter, motor and the like, and aims at using such cooling device for cooling a charging system.

Thus, according to the invention, there is provided a charging system for use with an electric vehicle, in which a primary coil unit provided in a charging coupler is excited by a power source for charging to thereby cause a secondary unit provided on the electric vehicle side to generate an electromotive force therein, and the battery device of the electric vehicle is charged by the thus generated electromotive force, characterized in that the primary coil unit or secondary coil unit is cooled by allowing a refrigerant of a cooling device provided in the electric vehicle to flow through the primary coil unit or secondary coil unit.

According to the above-mentioned structure, since the cooling device inherently provided in the electric vehicle can be used to cool the primary coil unit or secondary coil unit, there is eliminated the need for provision of a cooling device designed exclusively for the charging system.

The invention is also characterized in that the charging coupler includes a primary side refrigerant passage through which a refrigerant used to cool the primary unit is allowed to flow, and the receive portion of the electric vehicle, into which the charging coupler is to be mounted, includes a passage joint used to allow the primary side refrigerant passage to be in communication with the refrigerant passage of the above-mentioned cooling device when the charging coupler is mounted into the receive portion of the electric vehicle.

In the present structure, due to the fact that the refrigerant of the cooling device formed on the electric vehicle side flows through the passage joint to the primary side refrigerant passage formed on the primary coil unit side, the primary coil unit can be cooled by use of the cooling device provided on the electric car side.

Further, the invention is further characterized in that the charging coupler includes a heat transfer member for transferring heat generated in the primary coil unit to the receive portion side where the charging coupler is to be mounted, and the cooling device cools the heat transfer member to thereby be able to cool the primary coil unit.

In this structure, the heat generated in the primary coil unit can be transferred to the charging coupler receive portion side by means of the heat transfer member. And, since the cooling device cools the heat transfer member to thereby be able to cool the primary coil unit, there is obtained an effect that the primary coil unit can be cooled with no need for provision of a passage joint for flowing the refrigerant of the cooling device through the primary coil unit.

The invention is further characterized in that the primary coil or secondary coil is formed of a conductive pipe and the refrigerant of the cooling device is allowed to flow through the interior portion of the conductive pipe.

According to the present structure, because the coil is formed of the conductive pipe, the coil itself can be used as a portion of the refrigerant passage. As a result of this, the whole charging system can be made compact as well as a cooling operation can be carried out in the neighborhood of a source of heat generation, which leads to an excellent cooling efficiency.

DETAILED DESCRIPTION OF THE PREFERRED EMBODIMENTS

First Embodiment

Now, description will be given below of a first embodiment of a charging system for use with an electric vehicle according to the invention with reference to FIGS. 1 to 4.

Figure 1:
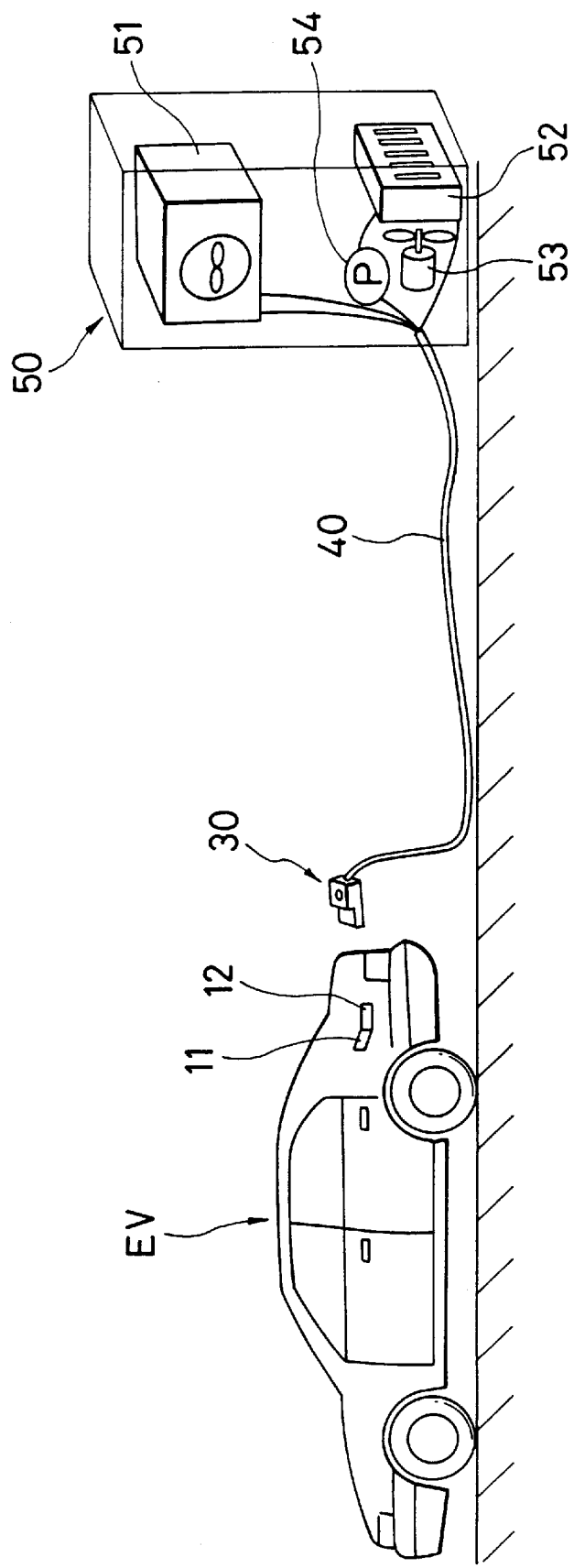
FIG. 1 is a schematic side view of a charging system according to the invention.
Figure 2:
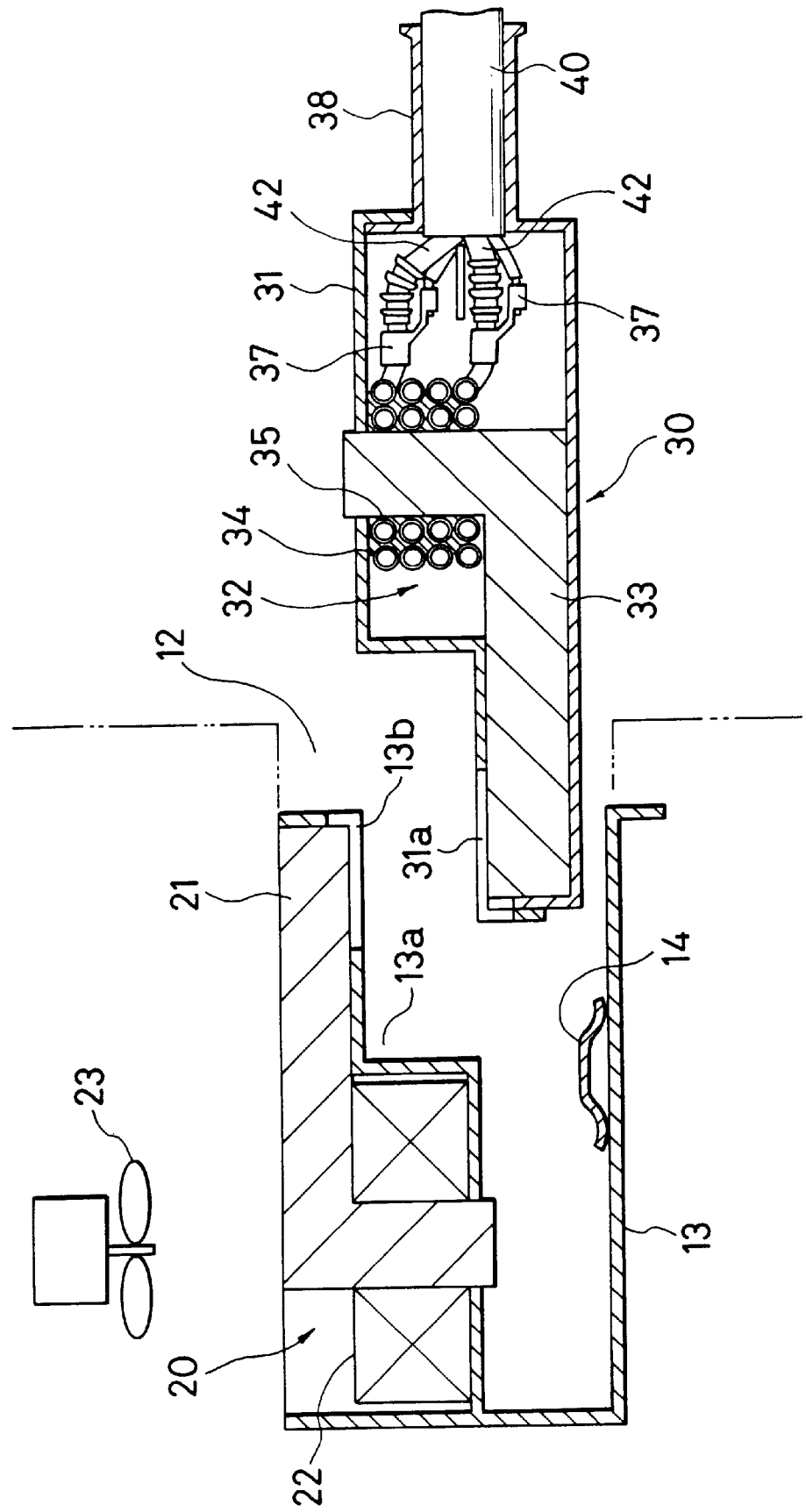
FIG. 2 is a longitudinal section view of a charging coupler and a receive portion employed in a first embodiment of a charging system according to the invention.

FIG. 1 shows the whole structure of the present charging system in which, in the outside portion of a vehicle body of an electric vehicle EV, there is provided a receive portion 12 that can be opened and closed, for example, by a cover 11, so that a charging coupler 30 to be described later can be inserted into and set in the receive portion 12. To the charging coupler 30, there is connected a power cable 40 for charging which is in turn connected to a charging unit 50. The charging unit 50 includes a high-frequency power source 51 for outputting a high-frequency voltage of, for example, 100 kHz, an air cooling type of radiator device 52 for radiating the heat of cooling water used as a refrigerant to be described later, and a air cooling fan 53 for the radiator device 52.

A coupler receive case 13, which defines a recessed portion 13a open toward the outside, is mounted on the receive portion 12 of the electric vehicle EV and a secondary coil unit 20 is disposed in the coupler receive case 13. The secondary coil unit 20 is composed of a secondary side core 21 formed of ferrite or the like and a secondary coil 22 wound around the secondary side core 21. The output terminal of the secondary coil 22 is connected to a charging circuit used to charge a power battery (not shown) serving as a power battery device of the electric vehicle EV, so that a high-frequency electromotive force induced by the secondary coil 22 can be rectified and used to charge the power battery.

The secondary side core 21 has a shape which can be produced by bending a quadrangular prism into an L shape. With the long side of the L shape arranged horizontally, the secondary side core 21 is fixed to the coupler receive case 13, while the short side of the L shape extends downwardly and the lower end portion thereof extends through the coupler receive case 13 and projects slightly into the recessed portion 13a. Also, the leading end side of the long side of the L shape extends through an opening 13b formed in the front end portion of the coupler receive case 13 and is exposed toward the interior portion of the recessed portion 13a. By the way, a plate spring 14 is mounted on the bottom portion of the recessed portion 13a of the coupler receive case 13, while the plate spring 14 is used to energize upwardly (toward the secondary coil unit 20) the charging coupler 30 which is inserted into the recessed portion 13a.

On the other hand, the charging coupler 30 is structured such that a primary coil 32 and a primary side core 33 are respectively stored in a housing 31. The primary side core 33 is identical in structure with the above-mentioned secondary side core 21, that is, with the long side of the L shape thereof extending along the interior portion of the housing 31, the primary side core 33 is fixed to the housing 31, while the short side of the L shape thereof extends upwardly on the base portion side of the housing 31, and the upper end face of the short side of the L shape extends through the housing 31 and projects externally. Also, the upper surface of the leading end portion of the long side of the L shape is exposed through an opening 31a formed in the front end portion of the housing 31. Therefore, when the charging coupler 30 is inserted into the recessed portion 13a of the receive case 13 of the electric vehicle EV, then the leading end upper surface of the long side portion of the primary side core 33 is opposed to the lower end face of the short side portion of the secondary side core 21, and the upper surface of the short side portion of the primary side core 33 is opposed to the lower surface of the leading end of the long side portion of the secondary side core 21. And, since the plate spring 14 provided in the bottom surface portion of the recessed portion 13a of the receive case 13 energizes the charging coupler 30 upwardly, the mutually opposed surfaces of the two cores 21 and 33 are brought into substantially contact with each other, so that a closed single-loop magnetic circuit is completed by the two cores 21 and 33.

In the short side portion of the primary side core 33, the primary coil 32 is formed by winding a conductive pipe 34 two or more times. In the present embodiment, this conductive pipe 34 is formed of a copper alloy and, referring to the dimensions thereof, for example, it has a diameter of 5 mm, a thickness of 0.5 mm, and an inside winding diameter of approx. 25 mm. Also, heat transferable silicone grease 35 is applied on the inner peripheral side of the primary coil 32, that is, between such side and the primary side core 33 to thereby enhance the heat transfer property between the primary side core 33 and primary coil 32 when compared with a condition in which the silicone grease 35 is not applied between them, so that the primary coil 32 is wound around the primary side core 33 in a heat transferable manner. By the way, although not shown, an enamel coating or the like is applied on both of the inner and outer surfaces of the conductive pipe 34 for insulation.

Figure 4:
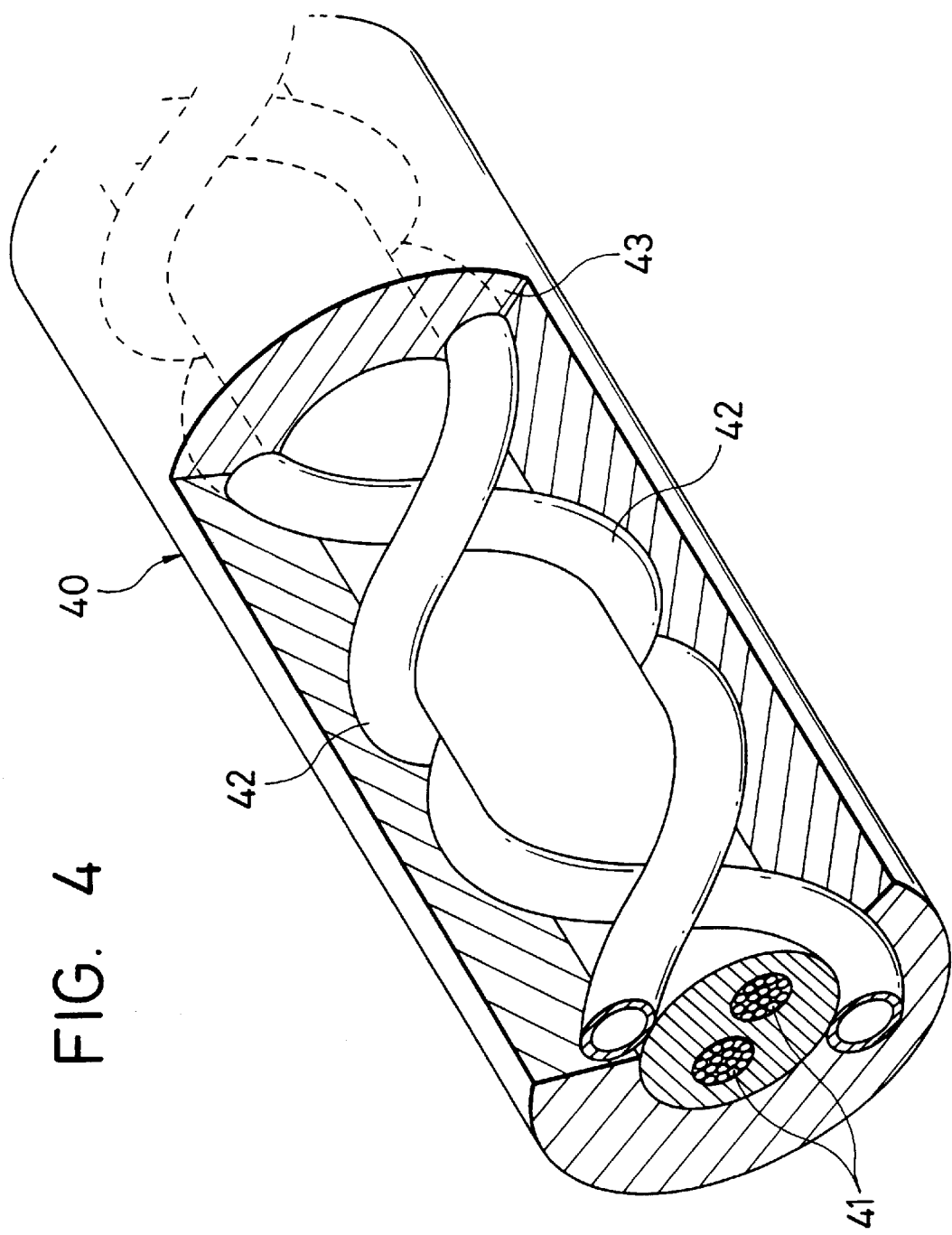
FIG. 4 is a partially broken perspective view of a charging power cable.

Also, as shown in FIG. 4, the above-mentioned charging power cable 40 includes two core wires 41; two refrigerant supply pipes 42 respectively forming the forward passage side and the backward or return passage side of the refrigerant supply passage are wound around the outer peripheral sides of the two core wires 41 through insulation layers in the mutually reversed spiral shapes; and, an outer cover layer 43 is applied to the outer periphery of the thus wound refrigerant supply pipes 42, thereby forming the whole of the charging power cable 40 as an integral body. By the way, each of the refrigerant supply pipes 42 is formed of heat resisting and flexible synthetic resin such as silicone resin or the like. And, the two core wires 41 of the charging power cable 40, on the charging unit 50 side, are respectively connected to the output terminals of the high-frequency power source 51; and, the forward passage side refrigerant supply pipe 42 is coupled to a circulation pump 54 provided within the charging unit 50, while the return passage side refrigerant supply pipe 42 is coupled to the radiator device 52.

Figure 3:
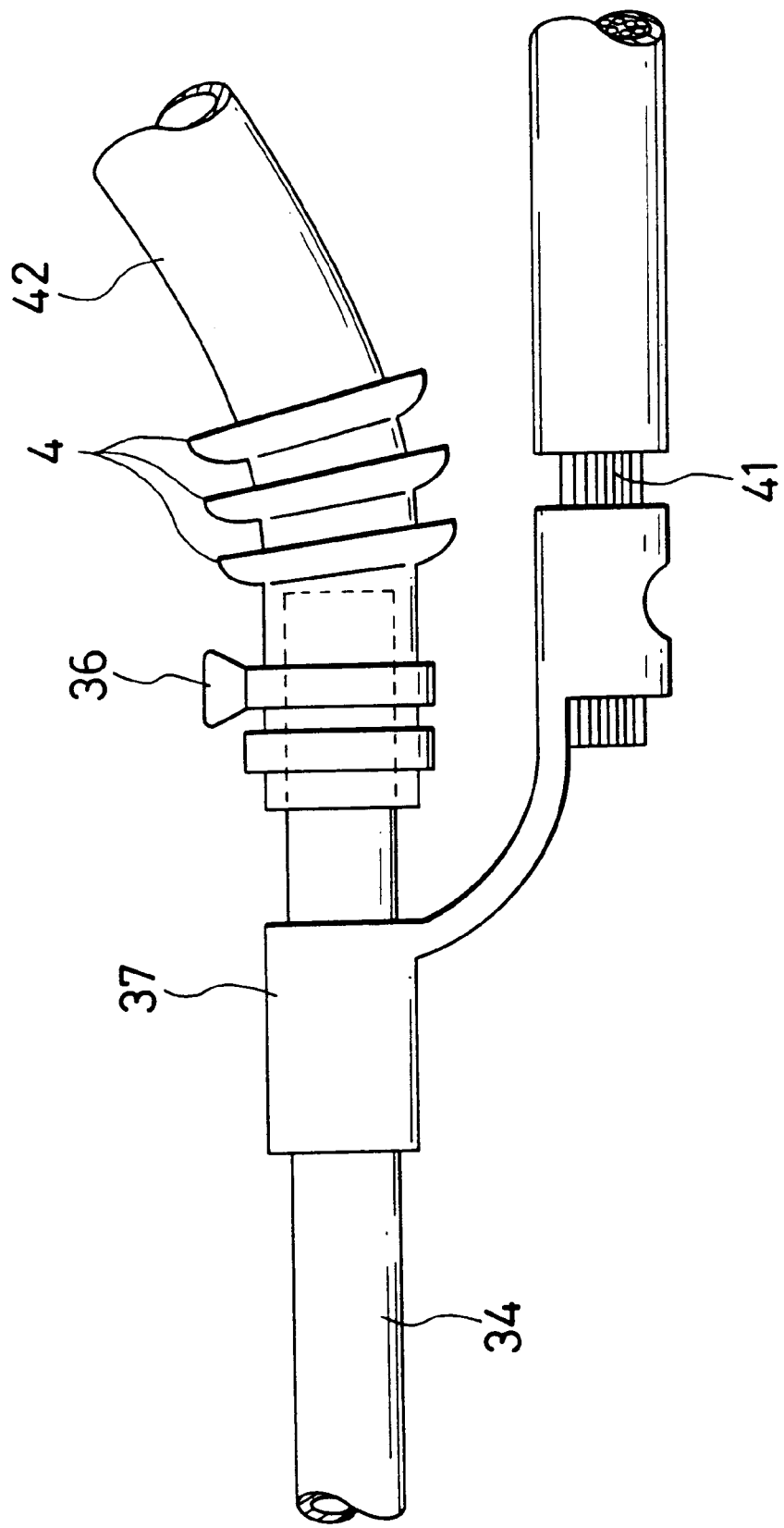
FIG. 3 is an enlarged side view of a connecting portion for a conductive pipe employed in the first embodiment.

And, a connecting structure for connecting the primary coil 32 and charging power cable 40 is as shown in FIG. 3. That is, the refrigerant supply pipes 42 are fitted with the end portion of the conductive pipe 34, while the thus fitted refrigerant supply pipes 42 are connected to the conductive pipe 34 by means of a pipe clamp 36 in a watertight manner. As a result of this, the conductive pipe 34, refrigerant supply pipes 42 and radiator device 52 cooperate together in forming a closed refrigerant circulation passage, and cooling water is poured into the closed refrigerant circulation passage as a refrigerant. Also, a plurality of water drain shades 44 are formed integrally in the connecting end portions of the refrigerant supply pipes 42. That is, even when water drops are caused to flow from the conductive pipe side due to dew condensation or the like, or, on the contrary, even when water drops flow from the refrigerant supply pipes 42 side, the water drain shades 44 prevent the water drops from flowing to the opposite side. By the way, out of the two refrigerant supply pipes 42, the forward passage side refrigerant supply pipe 42 is connected to the end portion of the conductive pipe 34 which provides the inner peripheral side of the primary coil 32, while the return passage side refrigerant supply pipe 42 is connected to the end portion of the conductive pipe 34 which provides the outer peripheral side of the primary coil 32, so that the cooling water is allowed to flow from the inner peripheral side of the primary coil 32 toward the outer peripheral side thereof.

Also, an energizing terminal 37 is connected by brazing or the like to the portion of the conductive pipe 34 that is located near the connecting portion thereof with the refrigerant supply pipe 42, while the core wires 41 of the charging power cable 40 are fixed to the energizing terminal 37 by staking. By the way, on the charging coupler 30 side, the charging power cable 40 is guided externally through a cylindrical portion 38 (serving also as a handle) which is provided integrally on and projected from the base portion side of the housing 31.

The present embodiment is structured in the above-mentioned manner and now the description will be given below of the operation of the present embodiment. When charging the electric vehicle EV, at first, the charging coupler 30 is inserted into the receive portion 12 of the vehicle body. As a result of this, the charging coupler 30 is inserted up to the deepest portion of the receive case 13 and, within the receive case 13, the charging coupler 30 is pressed against the secondary coil unit 20 side thereof by the plate spring 14, so that the two cores 21 and 33 are brought into contact with each other, thereby completing a closed-loop magnetic circuit. Then, if a power switch (not shown) provided in the charging unit 50 is switched on, then the circulation pump 54 and air-cooling fan 53 are actuated as well as the high-frequency power source 51 is operated, so that a high-frequency voltage is applied to the primary coil 32 through the charging power cable 40. That is, since the primary coil 32 is excited in this manner, an electromotive force is generated in the secondary coil 22, with the result that the power battery of the electric vehicle EV can be charged due to the thus generated electromotive force.

Because the high-frequency current flows through the primary coil 32, the conductive pipe 34 itself, which forms the primary coil 34, and the primary side core 33 are respectively caused to generate heat. However, as described above, since the circulation pump 54 is in operation in linking with the charging operation, there is produced a refrigerant circulation flow in which the refrigerant or the cooling water flows within the conductive pipe 34 through the forward side refrigerant supply pipe 42 of the charging power cable 40 and the cooling water is returned again from the radiator device 52 to the circulation pump 54 through the return side refrigerant supply pipe 42 of the charging power cable 40. Due to this, the heat generated in the conductive pipe 34 is immediately transferred to the cooling water flowing through the interior portion of the conductive pipe 34 and thus the heat is carried by the cooling water to the radiator device 52 side, where the cooling water is cooled by the air-cooling fan 53 and is then circulated again. For this reason, even if the conductive pipe 34 generates a large quantity of Joule heat during the charging operation, the conductive pipe 34 can be cooled at once, thereby being sure to prevent the primary coil 32 from rising in temperature greatly. Also, the heat generated in the primary side core 33 is transferred to the conductive pipe 34 forming the inner peripheral side of the primary coil 32 and thus the heat is similarly carried to the radiator device 52 by the cooling water flowing through the conductive pipe 34. Therefore, generation of excessive heat in the primary side core 33 can also be prevented positively.

By the way, heat generated in the secondary coil unit 20 is cooled by the air-cooling fan 23 that is provided within the vehicle body of electric vehicle.

As has been described heretofore, according to the present embodiment, there can be obtained the following effects:

(1) Since the primary coil 32 is formed of a conductive pipe and the cooling water flows through the interior portion of the primary coil 32, the coil conductor itself, which is a source of generation of Joule heat, can be cooled from the inside thereof, so that the primary coil 32 can be cooled with very high efficiency. Also, because the present embodiment employs a water cooling system in which the cooling water is allowed to circulate through the refrigerant supply pipe 42, when compared with a conventional air cooling system in which only the open air is ventilated, there can be obtained a high cooling efficiency, so that the charging coupler 30 can be made compact and can be increased in capacity.

By the way, in the present embodiment, a high-frequency current of 100 kHz is allowed to flow through the primary coil 32, while the depth of the current due to a skin effect can be computed as approx. 0.3 mm from the surface of the primary coil 32. For this reason, even if the coil conductor is formed hollow, there is no possibility of the electric resistance increasing, that is, the hollow coil conductor structure does not result in the lowered efficiency and heat generation. Or rather, according to the present embodiment, the hollow structure is used cleverly to thereby be able to realize an effective cooling operation.

(2) Due to the fact that the silicone grease 35 is filled up between the primary coil 32 and primary side core 33 to thereby allow the primary coil 32 to be wound around the primary side core 33 in a heat transferable manner, the heat generated in the primary side core 33 is also smoothly transferred to the conductive pipe 34 and is cooled here, thereby being able to prevent an increase in the temperature of the primary side core 33 effectively.

(3) Because the refrigerant supply pipe 42 is wound around the outer peripheries of the core wires 41 and is thereby formed integrally with the charging power cable 40, not only the cooling of the core wires 41 is possible but also the charging operation can be carried out simply by handling a single cable or the charging power cable 40, thereby being able to simplify the charging operation. Also, since there is employed a structure in which the radiator device 52 is incorporated in the charging unit 50, the whole of the charging facilities can be made compact. Further, due to the fact that the cooling water is circulated while it is cooled by the radiator device 52, there is eliminated the wasteful use of the refrigerant, which results in the economical use of the refrigerant.

(4) Moreover, since the cooling water is allowed to flow from the inner peripheral side of the primary coil 32 toward the outer peripheral side thereof, the present embodiment fits in with the situation that the inner peripheral side of the primary coil 32 is present near the primary side core 33 and is thus easy to increase in temperature, so that the whole of the primary coil 42 and primary side core 33 can be cooled efficiently and uniformly.

(5) In addition, use of the insulation layer on the inner peripheral surface of the conductive pipe 34 makes it possible to use water which has a conductive property. As a result of this, not only the cost of the material is low but also a relatively simple sealing structure can be used, which makes it possible to reduce the cost of the whole charging system.

However, according to the invention, the refrigerant is not always limited to water but, of course, various kinds of oils, hydrocarbon-system solvents such as CFC, and the like can also be used as the refrigerant.

Second Embodiment

Figure 5:
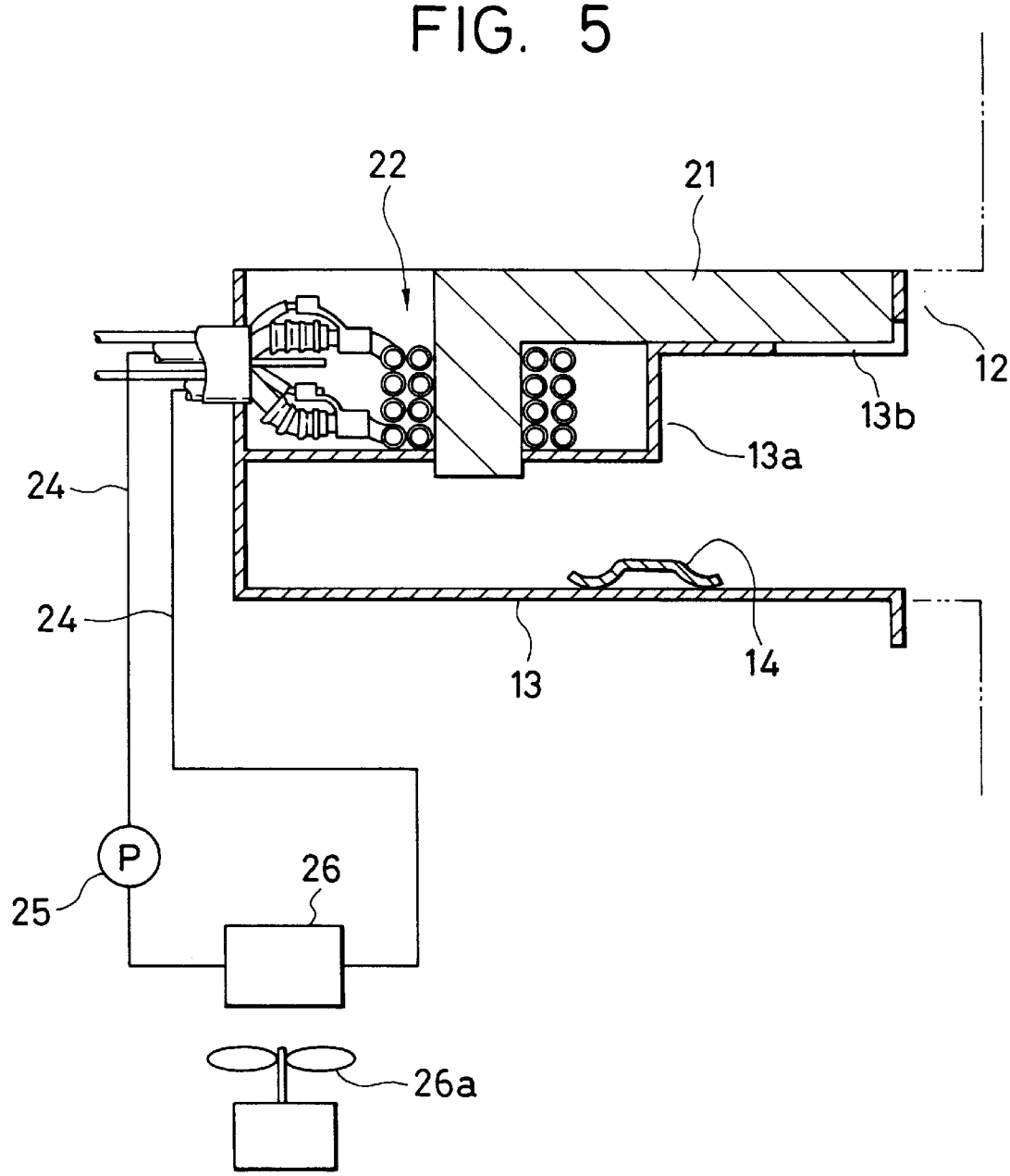
FIG. 5 is a longitudinal section view of a receive portion employed in a second embodiment of a charging system according to the invention.

Now, FIG. 5 shows a second embodiment of a charging system according to the invention, in which a cooling structure in the secondary coil unit 20 on the electric vehicle EV side is improved.

In the present embodiment, similarly to the primary coil 32, the secondary coil 22 is also structured by winding a conductive pipe, and cooling water as a refrigerant is allowed to flow through the interior portion of the secondary coil 22. Two refrigerant supply pipes 24 are connected respectively to the two ends of the above conductive pipe. That is, by operating a circulation pump 25, the cooling water is allowed to flow into the secondary coil 22 through the refrigerant supply pipe 24, while the heat of the cooling water is radiated in a radiator device 26 with a cooling fan 26a. With use of this structure, similarly to the primary side, the cooling of the secondary side can also be achieved efficiently. The remaining portions of the present embodiment are similar to the first embodiment and thus similar operation effects can be obtained.

Third Embodiment

Figure 6:
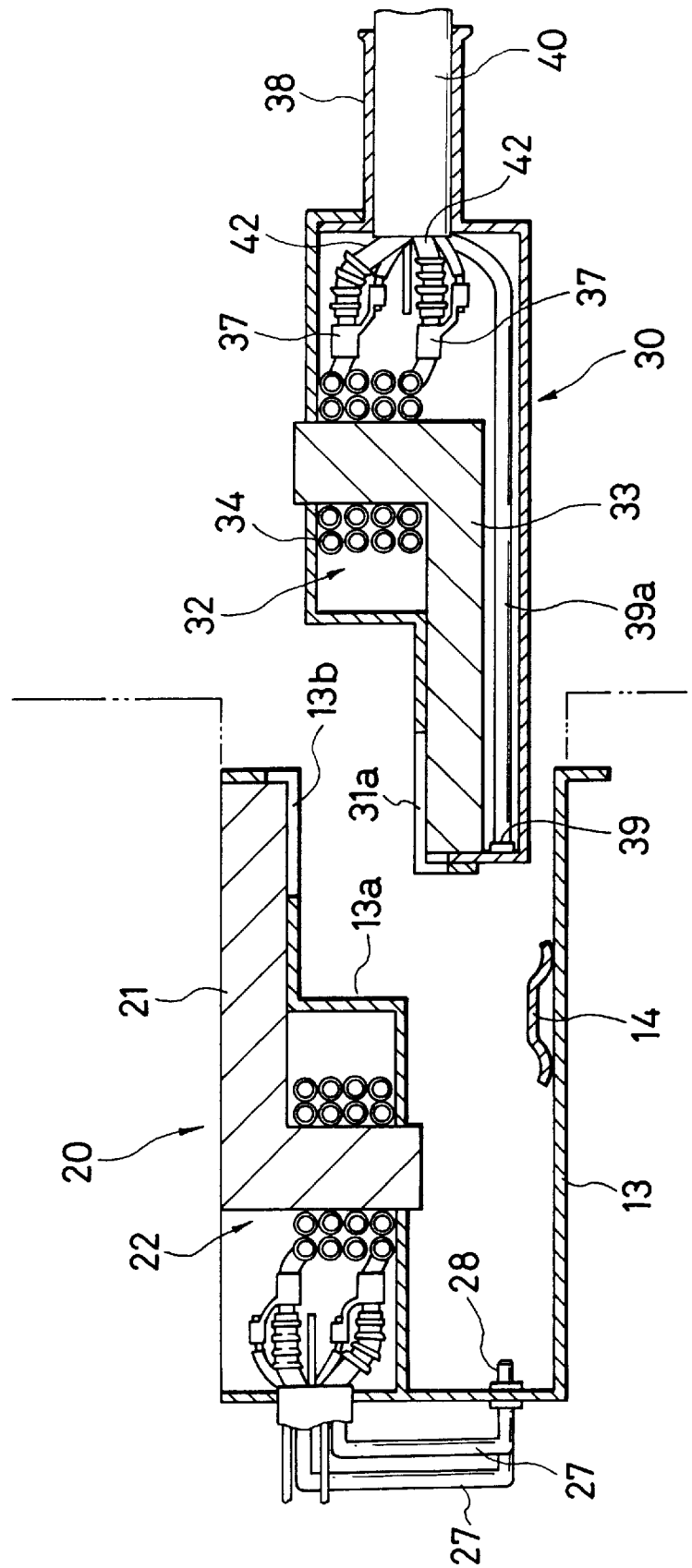
FIG. 6 is a longitudinal section view of a charging coupler and a receive portion employed in a third embodiment of a charging system according to the invention.

Now, FIG. 6 shows a third embodiment of a charging system according to the invention. In the present embodiment as well, the cooling structure of the secondary coil unit 20 is improved. Since the primary side structure of the present embodiment is similar to the first embodiment, the same parts are given the same reference characters and thus the description thereof is omitted here.

In the present embodiment, similarly to the primary coil 32, the secondary coil 22 is also structured by winding a conductive pipe, and cooling water as a refrigerant is allowed to flow through the interior portion of the secondary coil 22. Two refrigerant supply pipes 27 are connected respectively to the two ends of the above conductive pipe, while the refrigerant supply pipes 27 are connected respectively to two male-type joints 28 (only one of them is shown in FIG. 6) which are mounted on the deep-side wall of the coupler receive case 13. The two male-type joints 28 respectively correspond to two female-type joints 39 which are mounted on the leading end portion of the charging coupler 30 and, when the charging coupler 30 is inserted into the coupler receive case 13, then the male- and female-type joints are connected to each other, thereby completing a liquid passage. Also, when the two kinds of joints 28 and 39 are not connected with each other, valve mechanisms respectively incorporated in the joints 28 and 39 are closed to thereby prevent the liquid from flowing out from the joints 28 and 39. And, the female-type joints 39 on the charging coupler 30 side are connected through their respective auxiliary pipes 39a to their respective refrigerant supply pipes 42 which are integrally united with the charging power cable 40.

The charging power cable 40, on the charging coupler 30 side, is inserted through a cylindrical portion 38, which is provided integrally on and projected from the base end side of the housing 31 and is also used as a handle, and is further extended into the interior portion of the housing 31. And, the forward side and return side leading ends of the refrigerant supply pipes 42 are respectively made to fork into two branches within the charging power cable 40, and are mounted in the following manner.

The forward and return passages of one of the refrigerant supply pipes 42 are connected to the conductive pipe 34. The connecting structure is as shown in FIG. 3, that is, the refrigerant supply pipe 42 is fitted with the end portion of the conductive pipe 34 and is further connected in a watertight manner to the conductive pipe 34 by the pipe clamp 36. Also, a plurality of water drain shades 43 are formed integrally in the connecting end portion of the refrigerant supply pipe 42. That is, even when water drops are caused to flow from the conductive pipe 34 side due to dew condensation on the conductive pipe 34, or even when the water drops are caused to flow from the refrigerant supply pipe 42, the water drain shades 43 prevent the water drops from flowing in the opposite direction. Also, an energizing terminal 37 is connected by brazing or the like to the neighborhood of the connecting portion of the conductive pipe 34 with the refrigerant supply pipe 42, while the core wires 41 of the charging power cable 40 are fixed to the energizing terminal 37 by staking.

By the way, the forward passage side refrigerant supply pipe 42 is connected to the end portion of the conductive pipe 34 which provides the inner peripheral side of the primary coil 32, while the return passage side refrigerant supply pipe 42 is connected to the end portion of the conductive pipe 34 which provides the outer peripheral side of the primary coil 32, so that the cooling water is allowed to flow from the inner peripheral side of the primary coil 32 toward the outer peripheral side of the primary coil 32.

The remaining forward and return passages of the refrigerant supply pipes 42 are inserted through a space formed between the bottom wall of the housing 31 and the primary core 33 and are extended up to the leading end portion (see reference character 42a in FIG. 6) of the charging coupler 30, where they are connected to two female-type joints 39 (in FIG. 6, only one of them is shown) which are respectively mounted on the leading end wall of the housing 31 in such a manner that they extend through the housing 31 leading end wall. The female-type joints 39 are so disposed as to correspond to male-type joints 28 (to be described later) which are mounted on the deep-side wall of the receive portion 12. That is, if the charging coupler 30 is inserted into the coupler receive case 13, the two kinds of joints 28 and 39 are connected with each other, thereby being able to supply the cooling water into a connecting pipe 27 (to be described later) provided on the receive portion 12 side. Also, when the two kinds of joints 28 and 39 are connected with each other, valve mechanisms incorporated in the joints 28 and 39 are closed to thereby prevent the liquid, that is, the cooling water from flowing out from the joints 28 and 39.

On the other hand, on the receive portion 12 of the electric vehicle EV, there is mounted a coupler receive case 13 which defines a recessed portion 13a opening toward the outside, and a secondary coil unit 20 is disposed in the coupler receive case 13. The secondary coil unit 20 is structured in such a manner that a secondary coil 22 is wound around a secondary side core 21 which is formed of ferrite or the like and has the same shape as the above-mentioned primary core 33. The output terminal of the secondary coil 22 is connected to a charging circuit used to charge a power battery (not shown) serving as a power battery device of the electric vehicle EV, so that a high-frequency electromotive force induced by the secondary coil 22 can be used to charge the power battery after it is rectified. The secondary side core 21 is fixed to the coupler receive case 13 with the long side of the L shape thereof arranged horizontally, while the short side of the L shape extends downwardly and the lower end portion thereof extends through the coupler receive case 13 and projects slightly into the recessed portion 13a. Also, the leading end side of the long side of the L shape is inserted through an opening 13b formed in the front end of the coupler receive case 13 and is exposed toward the interior portion of the recessed portion 13a. Thus, if the charging coupler 30 is inserted into the recessed portion 13a of the coupler receive case 13 of the electric vehicle EV, the upper surface of the leading end portion of the long side portion of the primary core 33 is opposed to the lower end face of the short side portion of the secondary side core 21, and the upper surface of the short side portion of the primary core 33 is opposed to the lower surface of the leading end portion of the long side portion of the secondary side core 21. Also, a plate spring 14 is mounted on the bottom portion of the recessed portion 13a of the coupler receive case 13 and thus, if the charging coupler 30 inserted into the recessed portion 13a is energized upwardly (that is, toward the secondary coil unit 20 side), then the mutually opposing surfaces of the two cores 21 and 33 are contacted with each other, so that the two cores 21 and 33 complete a closed single-loop magnetic circuit.

The secondary coil 22 is structured in such a manner that a conductive pipe 24 similar to that of the primary coil 32 is wound around the short side portion of the secondary core 21 two or more times. Also, similarly to the primary coil unit 60, on the inner peripheral side of the secondary coil 22, between the inner peripheral side thereof and the secondary core 21, there is applied heat transferable silicone grease or the like.

Also, to the two ends of the conductive pipe 24, there are connected the respective one-side ends of a pair of connecting pipes 27 by means of the same structure as the above-mentioned connecting structure (see FIG. 3) between the conductive pipe 34 of the primary coil 32 and refrigerant supply pipe 42, whereas the other-side ends of the connecting pipes 27 are connected to two male-type joints 28 (in FIG. 6, only one of them is shown) which are respectively mounted on the deep-side wall of the coupler receive case 13. The male-type joints 28 project from the deep-side wall of the receive portion 12 toward the open portion of the coupler receive case 13 and are disposed at positions facing the above-mentioned female-type joints 39 in such a condition that the charging coupler 30 is energized upwardly of the receive portion 12 by the plate spring 14. Also, to the neighborhood of the connecting portion of the conductive pipe 24 with the above-mentioned refrigerant supply pipes 42, there are connected the energizing terminals 24a of the conductive pipes 24a by brazing or by similar connecting means, while the core wires of the power wires extending up to the power battery are fixed by staking to the energizing terminals 24a.

The present embodiment is structured in the above-mentioned manner and the operation thereof is as follows: That is, to charge the electric vehicle EV, at first, the charging coupler 30 is inserted into the receive portion 12 of the vehicle body of the electric vehicle EV. During such insertion, the charging coupler 30 is lifted up toward the secondary coil unit 20 with the mutually opposing surfaces of the two cores 21, 33 overlapped in part with each other, so that the mutually opposing surfaces of the two cores 21, 33 are contacted in part with each other, and, in this condition, the male-type joints 28 on the deep-side wall of the receive portion 12 are opposed to the female-type joints 39 on the front surface of the charging coupler 30. If the charging coupler 30 is pushed to the full while the mutually opposing surfaces of the two cores 21 and 33 are in sliding contact with each other, then the two kinds of joints 28 and 39 are inserted straight and are connected to each other during such pushing operation. As a result of this, not only the connecting pipes 27 are brought into communication with the refrigerant supply pipes 42 but also the mutually opposing surfaces of the two cores 21 and 33 are completely superimposed on each other, thereby completing a closed-loop magnetic circuit. Also, due to the above connection between the connecting pipes 27 and refrigerant supply pipes 42, a refrigerant passage passing within the conductive pipe 24 of 20 the secondary coil 22 is connected in parallel with a refrigerant passage passing within the conductive pipe 24 of the primary coil 32. Here, if a power switch (not shown) of the charging unit 50 is switched on, then not only the circulation pump 54 and air-cooling fan 53 are actuated but also the high-frequency power source 51 is operated, so that a high-frequency voltage is applied to the primary coil 32 through the charging power cable 40. Since the primary coil 32 is energized in this manner, there is generated an electromotive force of a high-frequency voltage in the secondary coil 22, with the result that the power battery of the electric vehicle EV can be charged due to the thus generated electromotive force.

Thus, a high-frequency current is now allowed to flow in each of the coils 32, 22, so that the conductive pipes 34, 24 themselves forming the respective coils 32, 22 as well as the cores 33, 21 are caused to generate heat. However, as described before, since the circulation pump 54 is in operation during the charging operation, the cooling water is allowed to flow within the conductive pipe 34 of the primary coil 32 through the forward passage side refrigerant supply pipe 42 of the charging power cable 40, and further flow from the refrigerant supply pipe 42 within the conductive pipe 24 of the secondary coil 22 through the two kinds of joints 39, 28 and connecting pipes 27. And, the cooling water is then allowed to flow further through the return passage side refrigerant supply pipe 42 of the charging power cable 40 and return from the radiator device 52 again to the circulation pump 54. That is, there is provided a circulation flow of a refrigerant. Due to such refrigerant circulation flow, heat generated in the conductive pipes 34 and 24 is immediately transferred to the cooling water flowing through the interior portions thereof and is thus carried to the radiator device 52 side, in which the cooling water is cooled by the air-cooling fan 53 and the thus cooled water is then circulated again. For this reason, even if there exists a situation that the conductive pipes 34 and 24 generate a large amount of Joule heat during the charging operation, the thus generated Joule heat is cooled immediately when it is generated, thereby being sure to prevent the two coils 32 and 22 from rising in temperature greatly. Also, when the two cores 33 and 21 generate heat, the heat is transferred to the conductive pipes 34 and 24 respectively forming the inner peripheral sides of the two coils 32 and 22 and, similarly to the above, the heat is then carried out to the radiator device 52 by the cooling water flowing through the conductive pipes 34 and 24.

In this manner, due to the fact that the circulation pump 54 of the charging unit 50 is operated according as the charging operation is started, the cooling water fed to the refrigerant supply pipes 42 is allowed to flow not only through the interior portion of the primary coil 32 but also through the interior portion of the secondary coil 22 of the secondary coil unit 20, thereby being sure to prevent the excessive heat generation of the two cores 33 and 21. As has been described heretofore, according to the present embodiment, there can be obtained the following effects:

(1) Even if a special cooling device is not provided on the electric vehicle EV side, the secondary coil 22 side can be cooled by use of the cooling system provided on the primary coil 32 side. This not only can simplify the structure of the electric vehicle EV side and reduce the weight thereof, but also can enhance the freedom of the design of the charging system.

(2) Since the radiator device 52 is incorporated in the charging unit 50, the whole of the charging facilities can be made compact. Also, due to the fact that the cooling water is circulated while it is cooled by the radiator device 52, there is eliminated the wasteful use of the refrigerant, so that the refrigerant or the cooling water can be used economically.

(3) Because the joints 28 and 39 are positioned such that they can be connected with each other in linking with the insertion operation of the charging coupler 30 into the receive portion 12, the joints 28 and 39 can be connected with each other automatically at the same time when a charging operation is carried out, which eliminates the need to execute a special operation to connect them. That is, the present embodiment is easy to operate.

(4) Since the coils 32 and 22 are respectively formed of conductive pipes and the cooling water is allowed to flow through the interior portions thereof, the coil conductor, which is a source of generation of Joule heat, can be cooled from the inside thereof, thereby being able to cool the coils 32 and 22 with very high efficiency.

By the way, in the present embodiment, a high-frequency current of 100 kHz is allowed to flow through the primary coil 32, while the depth of the current due to a skin effect can be computed as approx. 0.3 mm from the surface of the primary coil 32. For this reason, even if the coil conductor is formed hollow, there is no possibility of the electric resistance increasing, that is, the hollow coil conductor structure does not result in the lowered efficiency and heat generation. Or rather, according to the present embodiment, the hollow structure is used cleverly to thereby be able to realize an effective cooling operation.

(5) Since the cooling water is allowed to flow from the inner peripheral side of the primary coil 32 toward the outer peripheral side thereof, the present structure fits in with the situation that the inner peripheral side of the primary coil 32 is present near the primary side core 33 and is thus easy to increase in temperature, so that the whole of the primary coil 42 and primary side core 33 can be cooled efficiently and uniformly.

(6) Because the refrigerant supply pipe 42 is wound around the outer peripheries of the core wires 41 and is thereby formed integrally with the charging power cable 40, not only the cooling of the core wires 41 is possible but also the charging and cooling operation can be carried out simply by handling a single cable or the charging power cable 40, thereby being able to simplify the charging operation.

(7) Provision of the insulation layer on the inner peripheral surface of the conductive pipe 34 makes it possible to use water which has a conductive property. As a result of this, not only the cost of the material is low but also a relatively simple sealing structure can be used, which in turn makes it possible to reduce the cost of the whole charging system.

Fourth Embodiment

Figure 7:
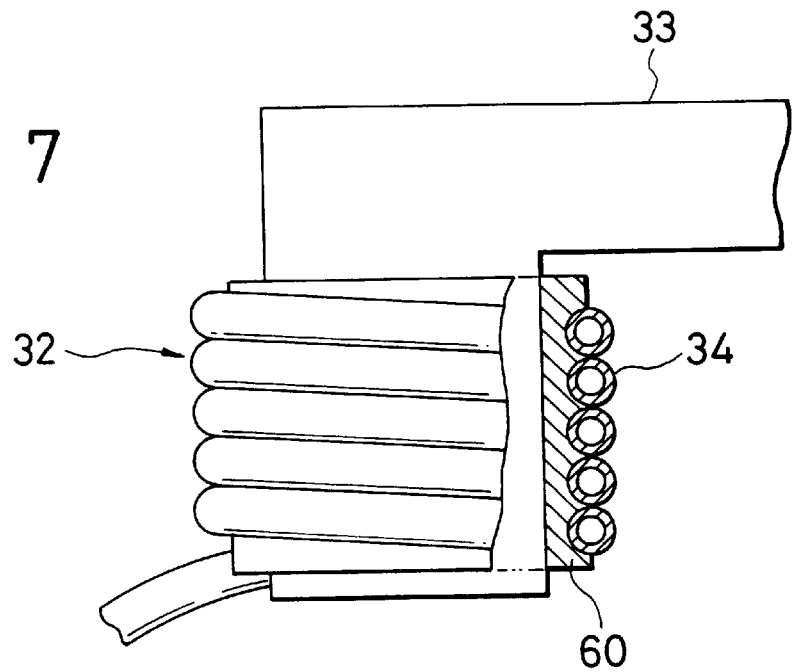
FIG. 7 is a partially broken side view of a primary coil unit employed in a fourth embodiment of a charging system according to the invention.
Figure 8:
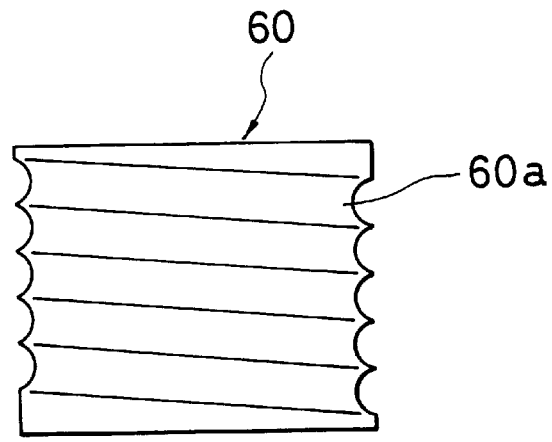
FIG. 8 is a side view of a bobbin employed in the fourth embodiment.

Now, FIGS. 7 and 8 show a fourth embodiment of a charging system according to the invention, which is different from the first embodiment in that the primary coil 32 is wound around a bobbin 60 which is vertically divided into two half sections, while the bobbin 60 is mounted on the primary side core 33.

Use of this structure not only can simplify the winding operation of the primary coil 32 but also can enhance the heat transferability between the primary coil 32 and core 33 to thereby contribute to a decrease in the temperature of the core 33. Also, in the outer periphery of the bobbin 60, there is formed a groove 60a that fits in with the outside diameter of the conductive pipe 34, which facilitates further the winding operation of the coil as well as increases the contact area between the conductive pipe 34 and bobbin 60 to thereby be able to enhance the cooling ability of the charging system.

As the material of the core 33, it is preferred to use material which has heat resistance, good conductivity, and an insulation property capable of restricting an eddy current loss as much as possible. For example, various kinds of ceramics such as ferrite, silicone nitride, alumina and the like, heat-resisting synthetic resin mixed with metal fillers, and the like are most suitable. However, other kinds of material can also be selected and used properly according to the specifications.

Fifth Embodiment

Figure 9:
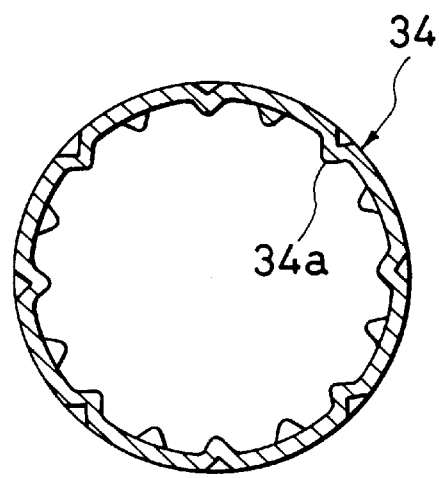
FIG. 9 is an enlarged section view of a conductive pipe employed in a fifth embodiment of a charging system according to the invention.

Now, FIG. 9 shows a fifth embodiment of a charging system according to the invention, in which the structure of the conductive pipe 34 is improved. The remaining portions of the fifth embodiment are similar to those of the first embodiment and thus the duplicate description thereof is omitted here.

The conductive pipe 34 is embossed from the outer peripheral side thereof using a pressing roller, for example, in the coil winding operation, thereby providing a large number of dimples 34a on the inner wall surface of the conductive pipe 34 in such a manner that they project slightly inwardly. By the way, the time of formation of the dimples 34a is not limited to the time when the coil is wound, but the dimples 34a may also be formed when the pipe is manufactured.

Provision of such dimples 34a not only increases the contact area between the conductive pipe 34 and the refrigerant flowing through the interior portion of the conductive pipe 34 but also causes turbulent flows in the flow of the refrigerant to thereby enhance the heat exchange efficiency between them. That is, the present embodiment provides an effect that the cooling efficiency can be improved.

Sixth Embodiment

Figure 10:
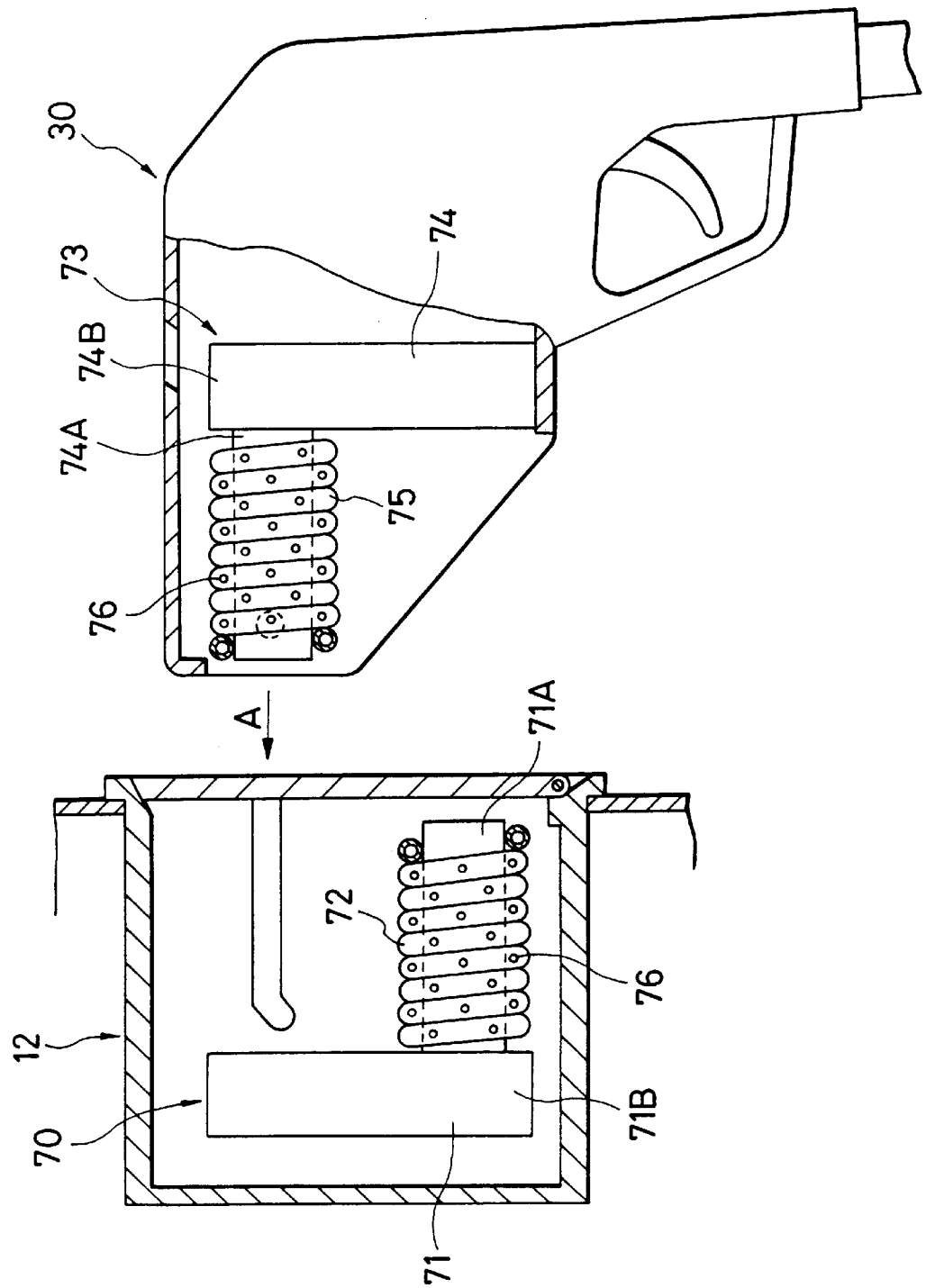
FIG. 10 is a longitudinal section view of a charging coupler and a receive portion employed in a sixth embodiment of a charging system according to the invention.
Figure 11:
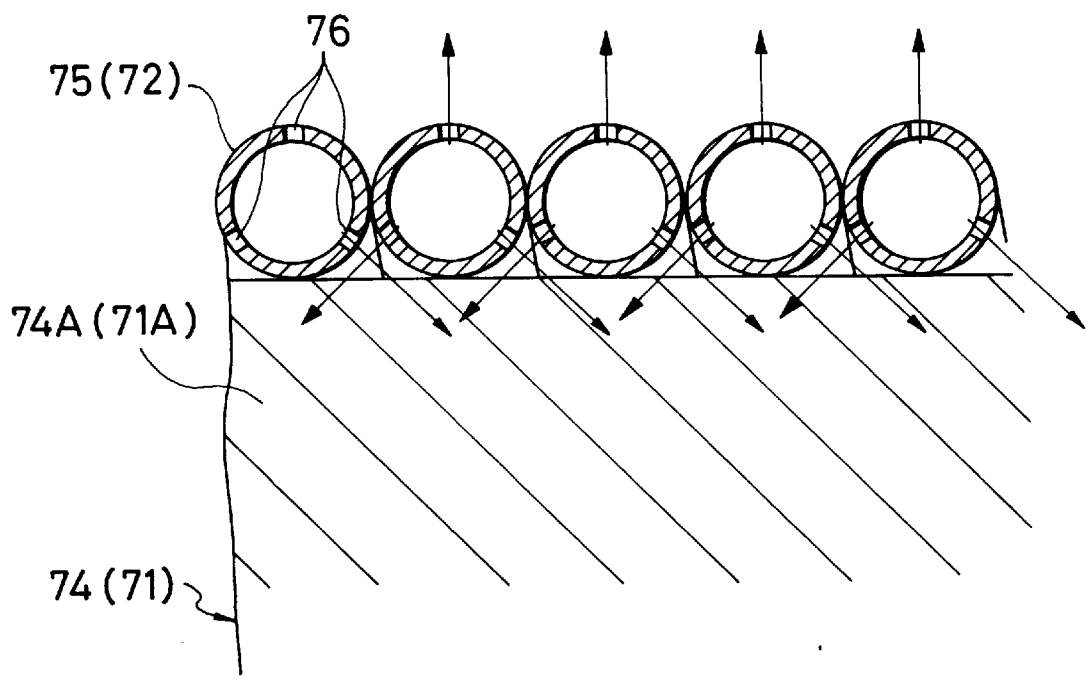
FIG. 11 is an enlarged side section view of a plurality of refrigerant discharge holes formed in a conductive pipe employed in the sixth embodiment.

Now, FIGS. 10 and 11 respectively show a sixth embodiment of a charging system according to the invention. The present embodiment is different from the above-mentioned respective embodiments in the structures of the primary and secondary coil units and, in particular, is characterized in that conductive pipes respectively forming the primary and secondary coils include a plurality of refrigerant discharge holes.

In the present embodiment, a secondary core 71 included in a secondary coil unit 70, as shown in FIG. 10, has an L shape when it is viewed from laterally, in which the horizontal side of the L shape extending along the mounting direction A (in FIG. 10, in the right and left direction) of the charging coupler 30 provides a cylindrical portion 71A having a circular cross section, while the vertical side of the L shape extending at right angles to the cylindrical portion 71A provides a prismatic portion 71B having a square cross section. And the leading end face (engaging surface) of the cylindrical portion 71A intersects the above-mentioned mounting direction A at right angles and the side surface (engaging surface) of the prismatic portion 71B similarly intersects the mounting direction A at right angles. A secondary coil 72 is structured in such a manner that a conductive pipe is wound two or more times in a single-layer winding manner, and is wound around the cylindrical portion 71A of the secondary core 71.

Also, a primary core 74 and a primary coil 75 included in a primary coil unit 73 are identical in structure with the above-mentioned secondary core 71 and secondary coil 72. The cylindrical portion 74A of the primary core 74 extends in the mounting direction A, the prismatic portion 74B of the primary core 74 extends downwardly, and the primary coil 75 is wound around the cylindrical portion 74A.

And, if the primary and secondary cores 71 and 74 are engaged with each other, then there is completed a prismatic-frame-shaped closed-loop magnetic circuit between the two coils 72 and 75.

In the conductive pipes forming the primary and secondary coils 72 and 75, there are formed a plurality of refrigerant discharge holes 76 in such a manner that they extend through their respective pipes (see FIG. 11). And, the conductive pipes of the two coils 72 and 75 are respectively connected to a compressor (not shown) and, if the charging operation starts, then cool air (for example, the air existing outside the electric vehicle) is supplied into the conductive pipes and is pressurized there, so that the cool air is discharged from the refrigerant discharge holes 76. Also, the refrigerant discharge holes 76 are formed uniformly over the whole peripheral surfaces of the conductive pipes and thus the cool air is applied between the coils and cores as well as to the outside portions of the coils to thereby be able to cool the whole interior portion of the receive portion 12 or charging coupler 30. That is, according to the present embodiment, since the refrigerant is applied directly to the respective portions of the cores and the like to thereby cool them, a high cooling efficiency can be obtained.

Seventh Embodiment

Figure 12:
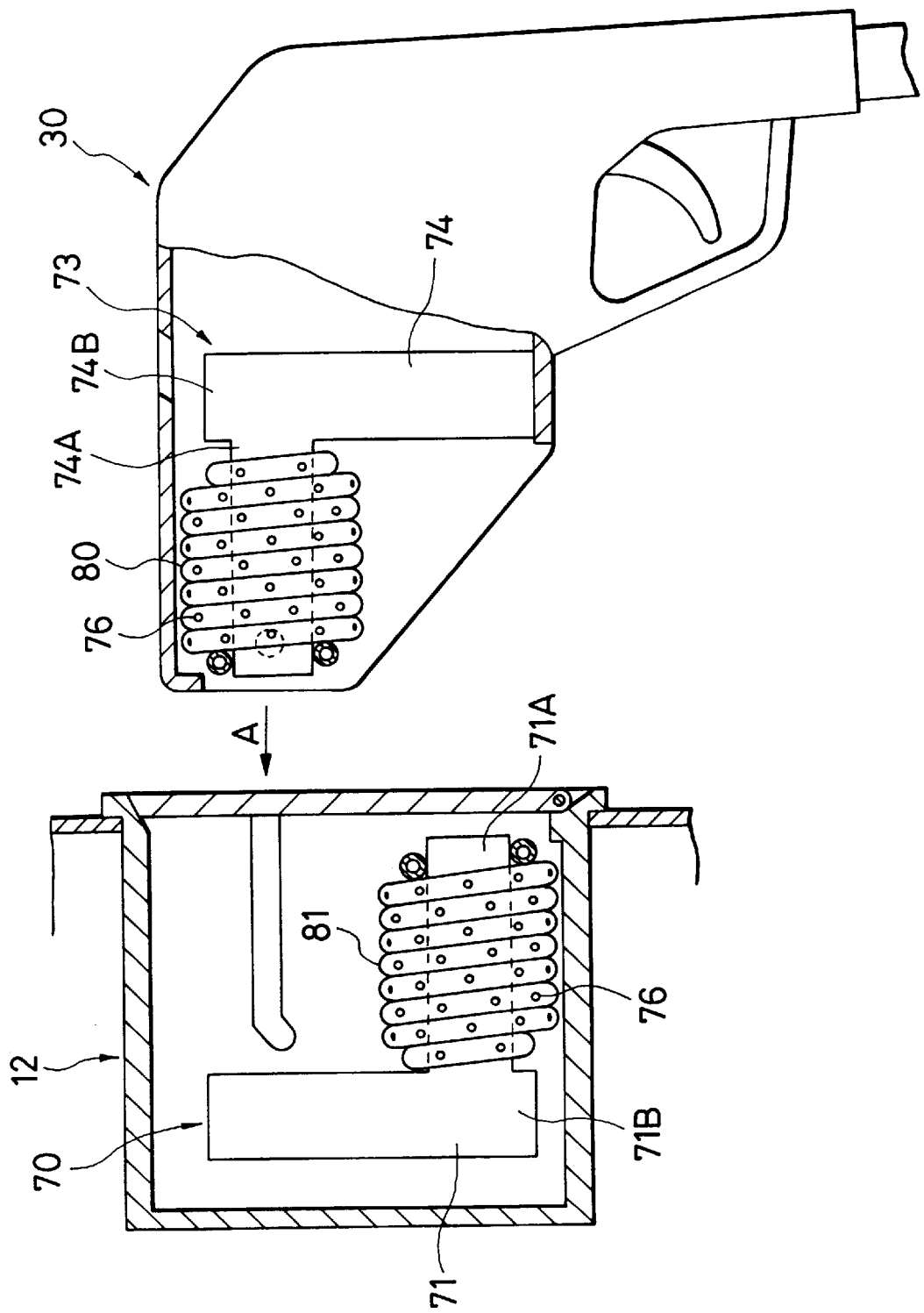
FIG. 12 is a longitudinal section view of a charging coupler and a receive portion employed in a seventh embodiment of a charging system according to the invention.
Figure 13:
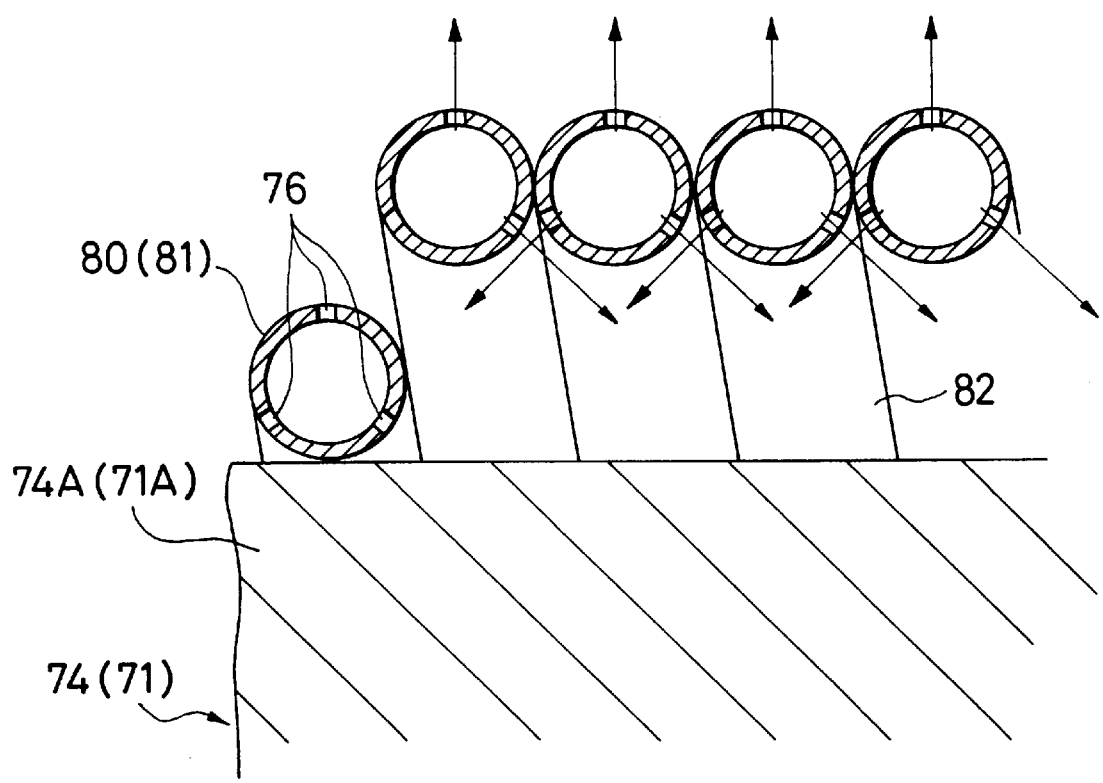
FIG. 13 is an enlarged side section view of a refrigerant discharge port of a conductive pipe employed in the seventh embodiment.

The present embodiment is shown in FIGS. 12 and 13 and is different from the sixth embodiment in the structures of the primary and secondary coils.

The primary and secondary coils 80 and 81, similarly to the sixth embodiment, are structured in such a manner that their respective conductive pipes are wound two or more times in a single-layer winding manner, and are wound around the cylindrical portions 74A and 71A of the cores 74 and 71. However, only the extreme end windings of the respective two end portions of the primary and secondary coils 80 and 81 are wound with a diameter corresponding to the outer peripheral diameters of the cylindrical portions 74A and 71A, whereas the other or intermediate windings of the intermediate portions thereof are wound with a diameter larger than the above diameter. Due to this, between the cores and coils, there are formed passage spaces 82 (see FIG. 13) which are used to flow the refrigerant therethrough. Provision of such passage spaces 82 facilitates the flow of the refrigerant between the coils and cores to prevent the stagnation of the refrigerant, thereby being able to enhance the cooling efficiency of the present charging system.

Eighth Embodiment

Figure 14:
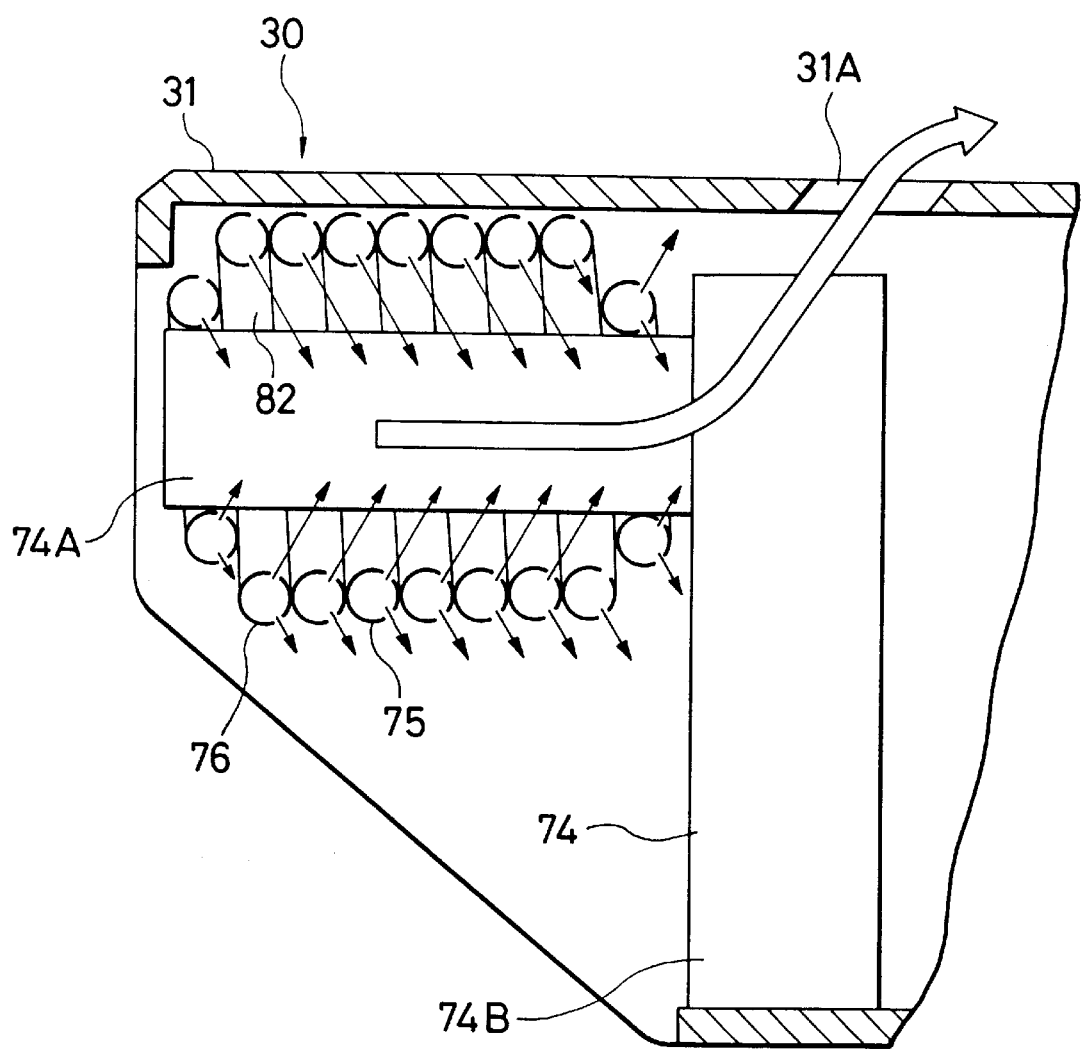
FIG. 14 is an enlarged side section view of a charging coupler employed in an eighth embodiment of a charging system according to the invention.

The present embodiment is shown in FIG. 14 and is a modified version of the seventh embodiment, in which the refrigerant discharge holes 76 are so formed as to face the backward side (in FIG. 14, the right side) of the charging coupler 30, so that the cool air is discharged from the refrigerant discharge holes 76 toward the back side of the charging coupler 30. Also, in the rear portion of the housing 31, there is formed a cool air exhaust hole 31A in such a manner that it extends through the housing rear portion, so that the air within the charging coupler 30 can be exhausted to the outside.

And, the cool air discharged from the refrigerant discharge holes 76 flows toward the right in FIG. 14 around the passage spaces 82 and coils 75, and is then exhausted from the cool air exhaust hole 31A externally of the charging coupler 30. Due to this, the warmed cool air can be exhausted positively and fresh cool air can be supplied to the respective portions, thereby being able to provide a high cooling efficiency.

Ninth Embodiment

Figure 15:
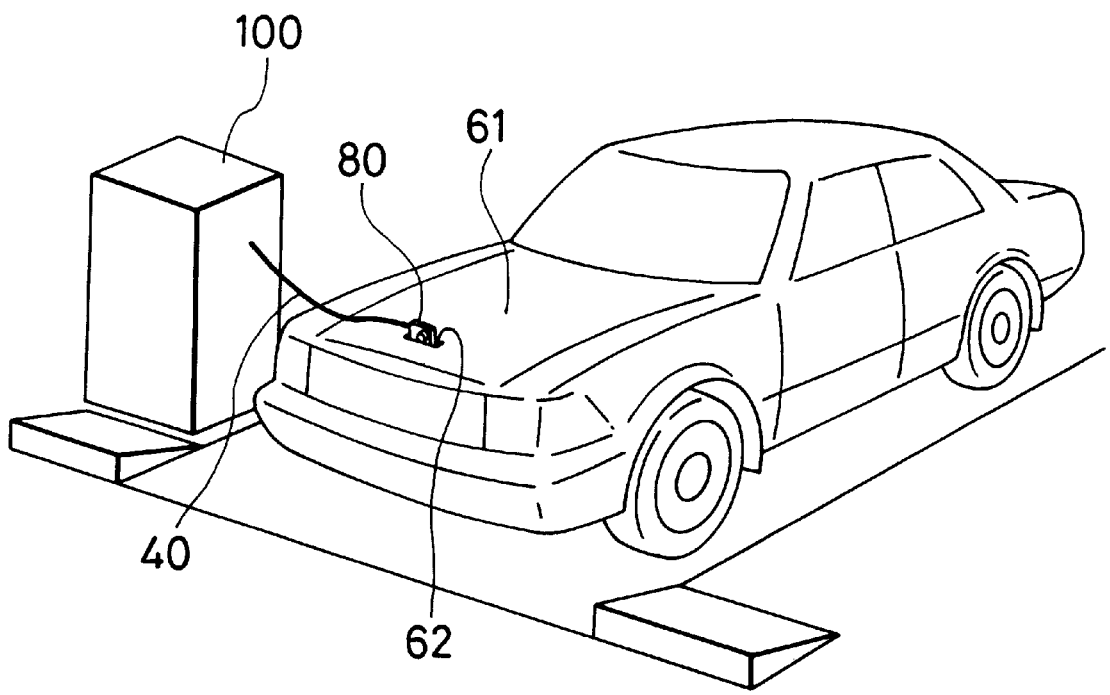
FIG. 15 is a schematic perspective view of a ninth embodiment of a charging system according to the invention.
Figure 16:
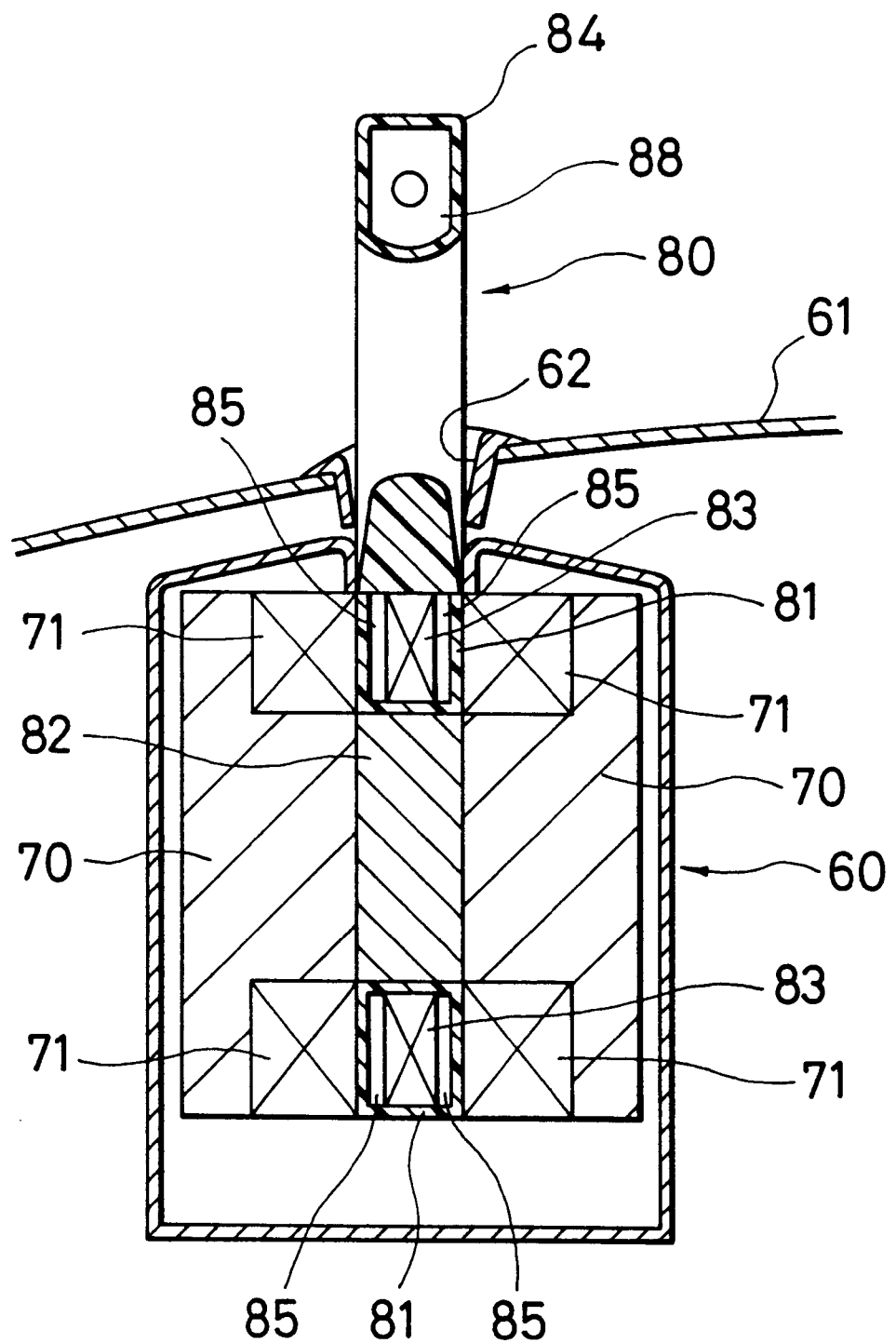
FIG. 16 is a longitudinal section view of the ninth embodiment, showing how to insert a charging coupler.
Figure 17:
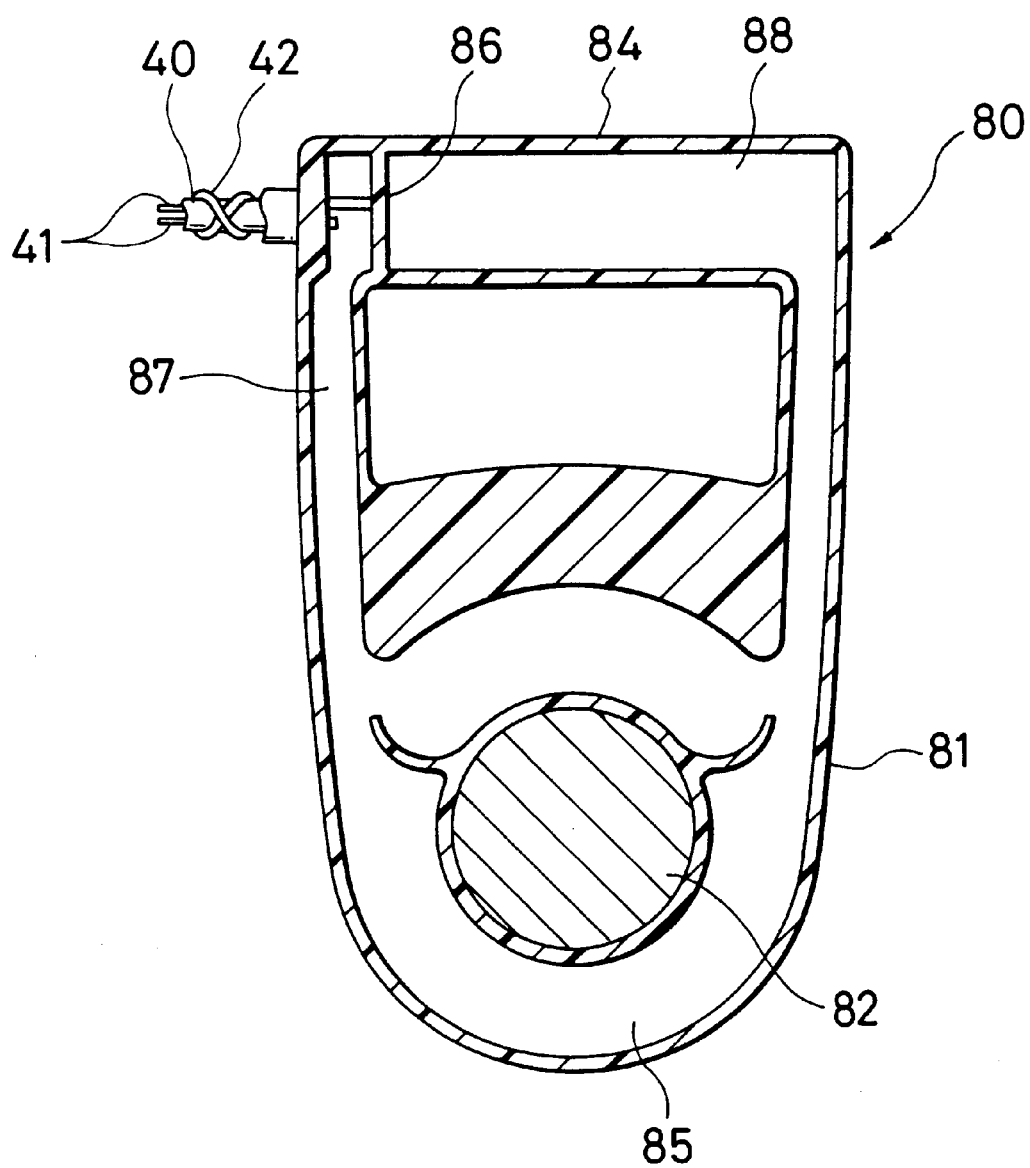
FIG. 17 is a section view of the charging coupler employed in the ninth embodiment.

Now, FIGS. 15 to 17 respectively show a ninth embodiment of a charging system according to the invention.

In the present embodiment, a receive portion 60 is formed in the front portion of the electric vehicle, while a charging coupler 80 can be inserted into the receive portion 60. The receive portion 60, as shown in FIGS. 15 and 16, is located downwardly of a slit 62 formed in the front portion of a hood 61 provided in the vehicle body of the electric vehicle and, similarly to the conventional charging structure, a pair of secondary side cores 70 are disposed opposed to each other, while the charging coupler 80 can be inserted between the two secondary side cores 70. Around the respective secondary side cores 70, there are wound their corresponding secondary coils 71 which are respectively connected to a charging circuit (not shown).

On the other hand, referring to the structure of the charging coupler 80, two primary coils 83 are wound around the periphery of a primary side core 82 and these members are stored in a housing 81 formed of resin, while a handle portion 84 is formed integrally with the charging coupler 80 (see FIGS. 16 and 17). To the handle portion 84, there is connected a charging power cable 40 which is identical in structure with one employed in the first embodiment. The core wires 41 of the charging power cable 40 are connected to the primary coils 83 which are wound around the periphery of the primary side core 82, so that power from a charging power source 50 can be supplied to the primary coils 83. While the charging coupler 80 is inserted into the receive portion 60, if a high-frequency current is applied from the charging power source 50 to the primary coils 83, then an electromagnetic induction phenomenon is caused to occur, so that power can be transmitted to the secondary coils 71 due to such electromagnetic induction phenomenon.

In the interior portion of the housing 81 of the charging coupler 80, as shown in FIG. 16, on the two sides thereof with the primary coils 83 between them, there is formed an annular refrigerant passage 85 which is insulated from the primary coils 83. This refrigerant passage 85 is connected with the handle portion 84 and is divided into an inflow side passage 87 and an outflow side passage 88 by a partition wall 86 formed within the hollow handle portion 84. The inflow side passage 87 is in communication with the forward passage side of the refrigerant supply tube 42 formed integrally with the charging power cable 40, whereas the outflow side passage 88 is in communication with the return passage side of the refrigerant supply tube 42.

In the above-mentioned structure, to charge the electric vehicle, the charging coupler 80 is inserted into the receive portion 60 through the slit 62 formed in the hood 61. And, similarly to the first embodiment, the primary coils 83 are excited and a pump is driven to thereby allow cooling water to circulate through the refrigerant circulation passage. Due to this, the cooling water flows from the forward passage side refrigerant supply tube 42, passes through the forward passage side refrigerant passage 85 formed within the housing 81 of the charging coupler 80, further through the return passage side refrigerant passage 85, and returns to the radiator device 52. During such circulating flow, the cooling water absorbs the heat of the primary coils 83 and primary side core 82 and thus rises in temperature, while the heat of the cooling water is radiated in the radiator device 52 within the charging power source 50. As a result of this, in the present embodiment as well, similarly to the first embodiment, the whole of the charging coupler 80 can be maintained at low temperatures.

Tenth Embodiment

Figure 18:
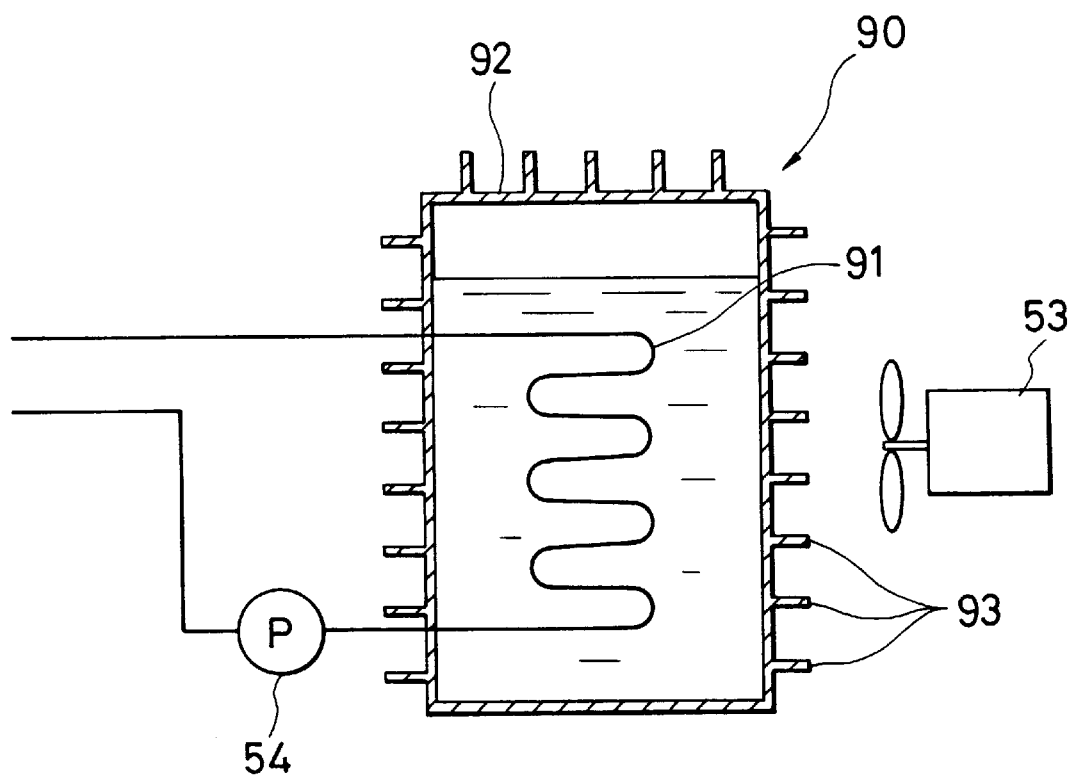
FIG. 18 is a section view of a radiator device employed in a tenth embodiment of a charging system according to the invention.

Now, FIG. 18 shows a tenth embodiment of a charging system according to the invention. The present embodiment is different from the above-mentioned respective embodiments in that the structure of a radiator device 90 is improved.

That is, between a return passage side refrigerant supply tube 42 provided in the charging power cable 40 and a forward passage side refrigerant supply tube 42, there is provided a radiation portion 91 made of a metal pipe which is formed in a meandering shape. Cooling water within the refrigerant supply tube 42 passes through the radiation portion 91 and is sent to the forward passage side refrigerant supply tube 42 by a circulation pump 54.

And, the radiation portion 91 is stored in the interior portion of a radiator tank 92, while a refrigerant having a low boiling point such as flon or the like is sealed in the interior portion of the radiator tank 92. On the outer periphery of the radiator tank 92, there are provided a large number of radiation fins 93 to which cooling air can be supplied from a cooling fan 53.

In the present structure, if the cooling water is circulated through the charging coupler by the circulation pump 54, then the low-boiling-point refrigerant is heated by the heated cooling water and is thereby caused to rise in temperature, while part of the thus heated refrigerant boils. Then, the boiling low-boiling-point refrigerant condenses and drops down onto the inner wall of the radiation tank 92, while the radiator tank 92 is cooled by the radiation fins 93. With use of this structure, it is possible to secure a sufficient radiation area in the radiator device 90, so that a cooling efficiency can be enhanced further.

Eleventh Embodiment

Now, an eleventh embodiment of a charging system according to the invention is shown in FIGS. 19 to 22. The present embodiment is similar in structure to the before described third embodiment except for the following points. Therefore, the same parts of the present invention as those of the third embodiment are given the same designations and thus the description thereof is omitted here, whereas description will be given below of only the different parts of the present structure.

Figure 19:
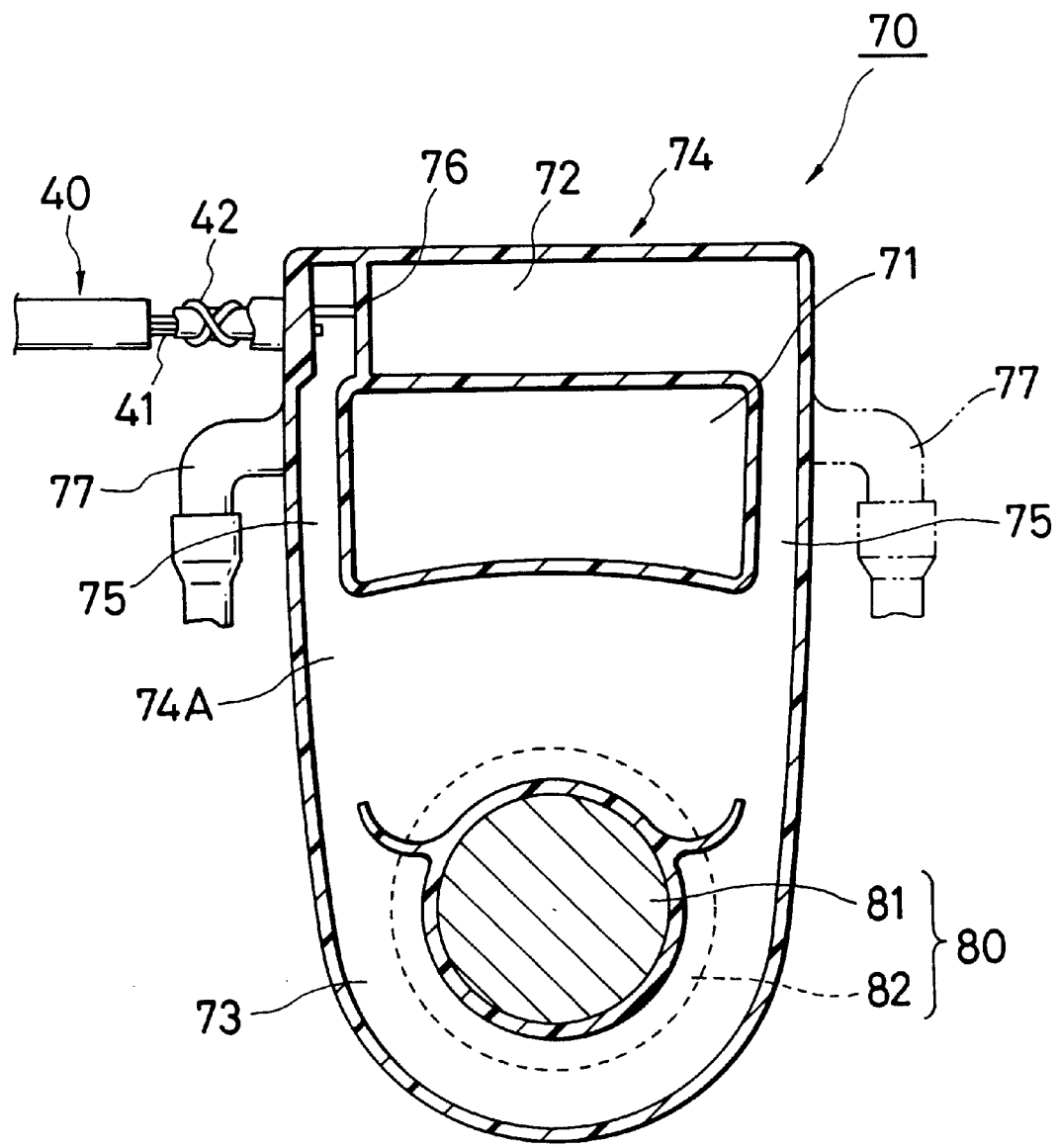
FIG. 19 is a section view of a charging coupler employed in an eleventh embodiment of a charging system according to the invention.

That is, a charging coupler 70, as shown in FIG. 19, is formed long in the vertical direction as a whole and includes a substantially rectangular hole 71 formed on the upper end side thereof in FIG. 19. And, the portion of the charging coupler 70 situated upwardly of the hole 71 provides a handle portion 72 by which an operator can hold the charging coupler 70, whereas the portion of the charging coupler 70 situated downwardly of the hole 71 provides a main body portion 73 which is to be inserted into a receive portion 12 provided in the electric vehicle EV, with a primary coil unit 80 fixed to the main body portion 73.

Figure 20:
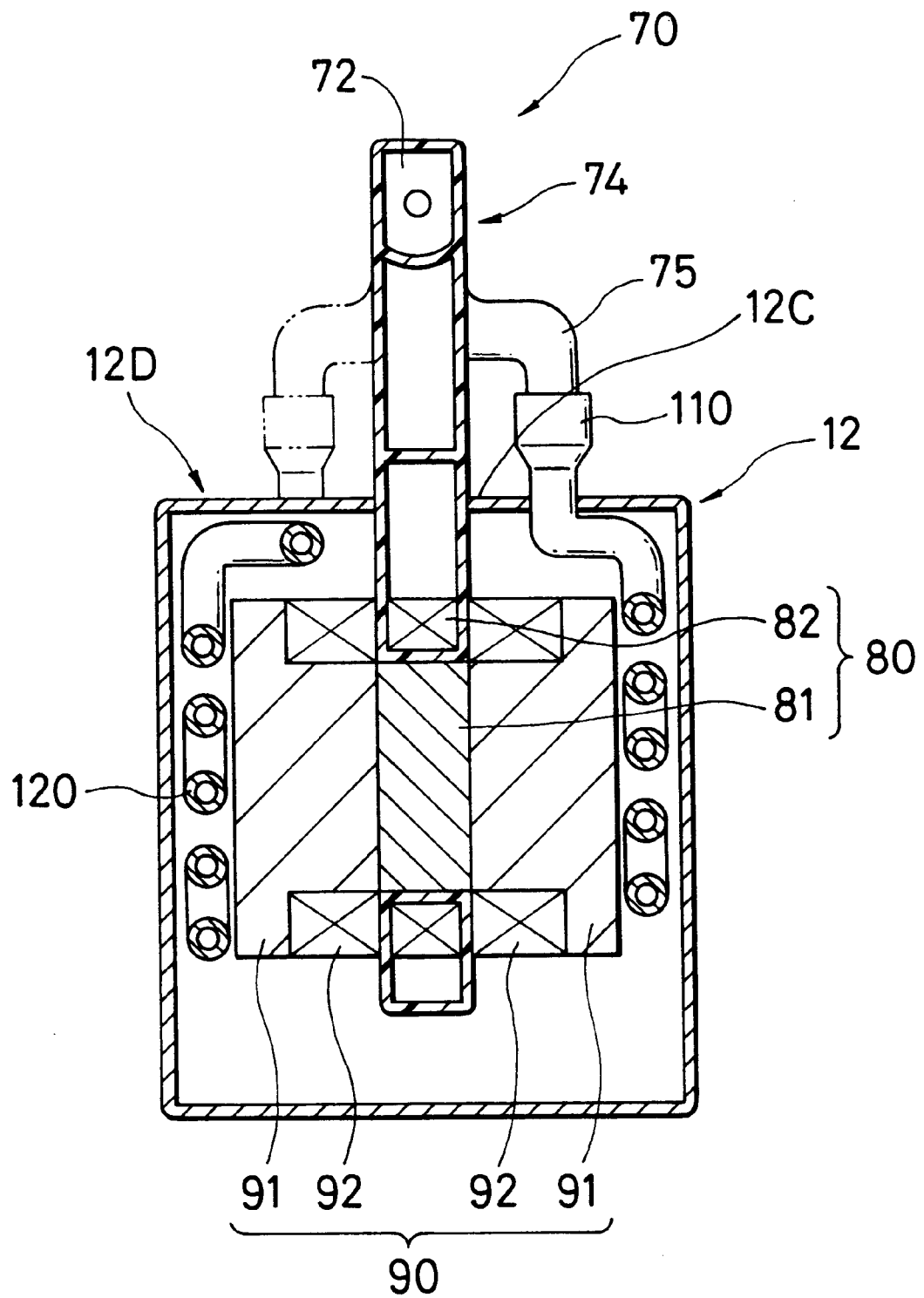
FIG. 20 is a section view of a charging coupler and a receive portion employed in the eleventh embodiment.

The primary coil unit 80 is composed of a primary core 81 which is formed of ferrite in a flat cylindrical shape, and a primary coil 82 formed of Litz wires or the like and wound around the peripheral surface of the primary core 81. And, as shown in FIG. 20, while the two end faces of the primary core 81 thereof are exposed, the primary coil unit 80 is fixed to a housing 74 provided in the charging coupler 70.

The housing 74 is wholly formed in a hollow shape with the interior portion thereof closed, while the hollow portion of the housing 74 provides a refrigerant passage 74A which allows cooling water to flow therethrough without leaking externally of the charging coupler 70. Referring to the concrete structure of the refrigerant passage 74A, the hollow portion of the handle portion 72 is connected in communication with the hollow portion of the main body portion 73 by the hollow portions of the right and left connecting portions 75 and 75 of the hole 71, and the hollow portion of the handle portion 72 is separated by a partition wall 76 which is provided near to the left in FIG. 19. And, a charging power cable 40 is mounted on the left side wall of the handle portion 72, and a refrigerant supply pipe 42 is extended from the charging power cable 40; and, the forward passage of the refrigerant supply pipe 42 extends through the left side wall of the handle portion 72 and is opened into the hollow portion situated on the left of the side wall of the handle portion 72 in FIG. 19, whereas the return passage of the refrigerant supply pipe 42 extends not only through the left side wall of the handle portion 72 but also through the partition wall 76 and is opened into the hollow portion situated on the right of the partition wall 76 in FIG. 19. Thanks to this structure, the cooling water is allowed to flow from the left connecting portion 75 in FIG. 19 to the main body portion 73, from the main body portion 73 to the right connecting portion 75, and further from there to the handle portion 72.

By the way, the core wires (not shown) of the charging power cable 40 are connected to the terminal of the primary coil 82 through a gap (not shown) existing outside a passage which is formed in the housing 74.

Figure 21:
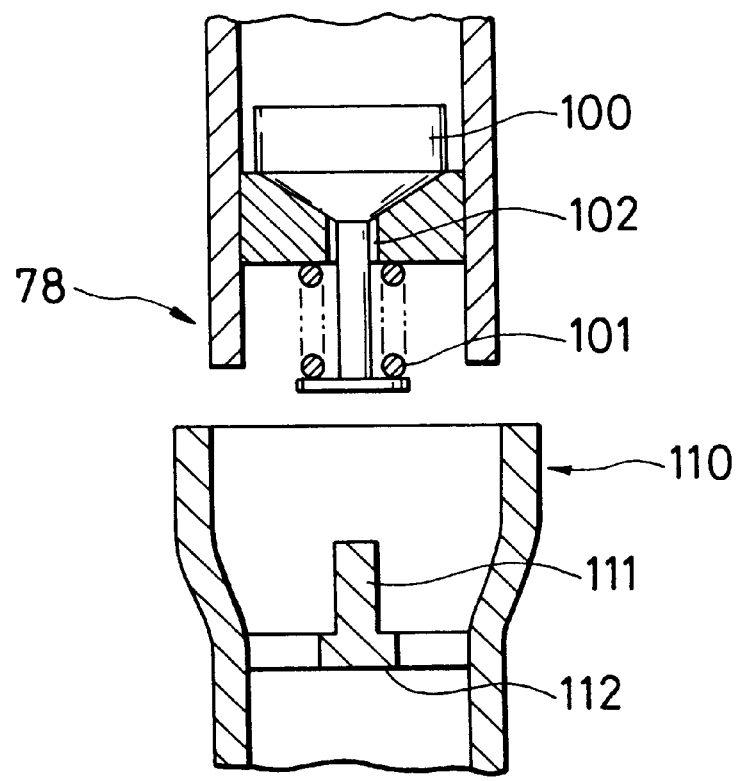
FIG. 21 is a section view of passage joints employed in the eleventh embodiment, showing a state before they are connected together.
Figure 22:
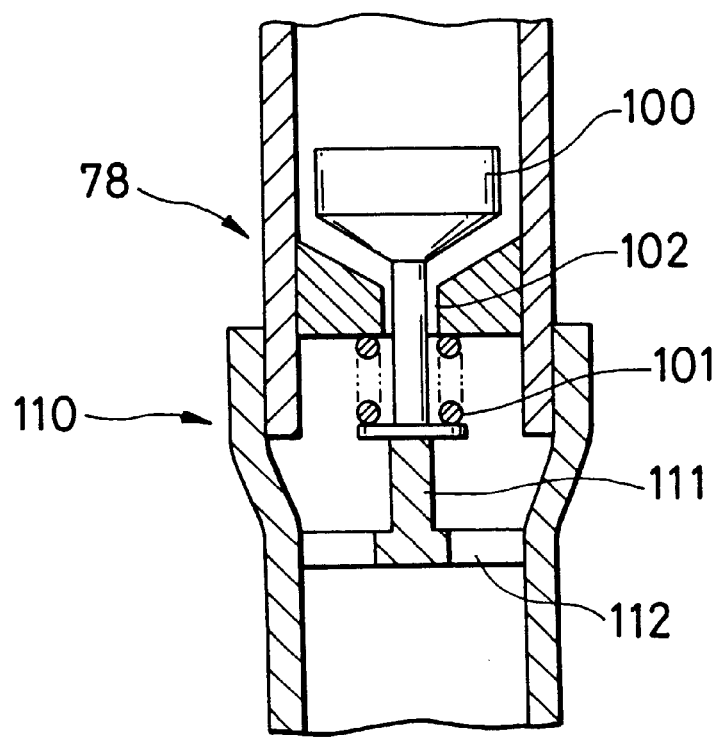
FIG. 22 is a section view of passage joints employed in the eleventh embodiment, showing a state after they are connected together.

Now, the connecting portions 75 respectively include branch passages 77 which are used to supply the cooling water to the passage formed on the receive portion 12 side, while the receive portion 12 will be discussed below. Each of the branch passages 77 rises laterally from the connecting portion 75 and is then bent downwardly, and the leading end portion of the branch passage 77 faces in a direction in which the charging coupler 70 is inserted into the receive portion 12, while a normally closed type of opening and closing valve 78 (which is shown in detail in FIGS. 21 and 22) is provided in the leading end portion of the branch passage. Referring now to the concrete structure of the opening and closing valve 78, as shown in FIGS. 21 and 22, a movable cover 100 is pressed against a small-diameter opening 102 (with the leading end thereof narrowed) by a compression spring 101; and, normally, the opening 102 is closed by the movable cover 100 (see FIG. 21) and, if the opening and closing valve 78 is inserted into a receive portion 110 to be described later, then the movable cover 100 is removed apart from the opening 102 by a projection III provided in the interior portion of the receive portion 110 (see FIG. 22), thereby allowing the cooling water to pass through the opening 102.

On the other hand, in the receive portion 12 of the electric vehicle EV, as shown in FIG. 20, there is mounted a coupler receive case 12D including an opening 12C opened externally and upwardly, while a secondary coil unit 90 is disposed in the interior portion of the c12D. The opening se 12D. The opening 12C corresponds to the shape of the cross section of the charging coupler 70, while the main portion 73 of the charging coupler 70 can be inserted into the coupler receive case 12D through the opening 12C.

The secondary coil unit 90 includes a pair of secondary cores 91 and 91 which are respectively formed of ferrite and are so disposed right and left as to be opposed to each other while a gap corresponding to the thickness dimension of a primary core 81 is present between them and, if the charging coupler 70 is set in the receive portion 12, then the exposed surface of the primary core 81 is caused to face the mutually opposed surfaces of the secondary cores 91 and 91. Also, secondary coils 92 formed of Litz wires are wound around the secondary cores 91 in such a manner that the axes thereof are matched to the mutually opposed direction thereof, and the output terminals of the secondary coils 92 are connected to a charging circuit which is used to charge a power battery (not shown) that is the battery device of the electric vehicle EV.

And, between the right and left secondary cores 91 and the side walls of the coupler receive case 12D, there is interposed a connecting pipe 120 which is used to cool the secondary coil unit 90. The connecting pipe 120 is formed by bending a single pipe which is formed of copper alloy. In particular, the two end portions of the connecting pipe 120 are fixed to the upper surface wall of the coupler receive case 12D, whereas the intermediate portion thereof is guided through the interior portion of the coupler receive case 12D in such a manner that it meanders on the side surfaces of the two secondary cores 91 and 91 in order to increase the contact area thereof with respect to the two secondary cores 91 and 91. The section of the meandering portion of the connecting pipe 120 is shown in FIG. 20.

The two end portions of the connecting pipe 120 are disposed in such a manner that they can correspond to the branch passages 77 of the charging coupler 70 when the charging coupler 70 is inserted into the opening, and the two end portions of the connecting pipe 120 further project upwardly from the upper surface wall of the coupler receive case 12D, while they include in the extreme end portions thereof receive portions 110 which can receive the above-mentioned opening and closing valve 78 therein. In the interior portion of the receive portion 110, a support plate 112 is extended from the inner peripheral surface thereof and the above-mentioned projection 111 is projected upwardly from the bottom portion of the support plate 112. Also, in the side portions of the support plate 112, there are formed through holes through which the cooling water is allowed to flow into the connecting or cooling pipe 120.

In the structure according to the present embodiment as well, similarly to the above-mentioned third embodiment, even if a special cooling device is not provided on the electric vehicle EV side, the secondary coil unit 90 can be cooled by use of the cooling system of the primary coil unit 80, which makes it possible not only to simplify the structure of the electric vehicle EV side but also to reduce the weight thereof.

Twelfth Embodiment

Now, description will be given below of a twelfth embodiment of a charging system according to the invention with reference to FIGS. 23 to 25.

Figure 23:
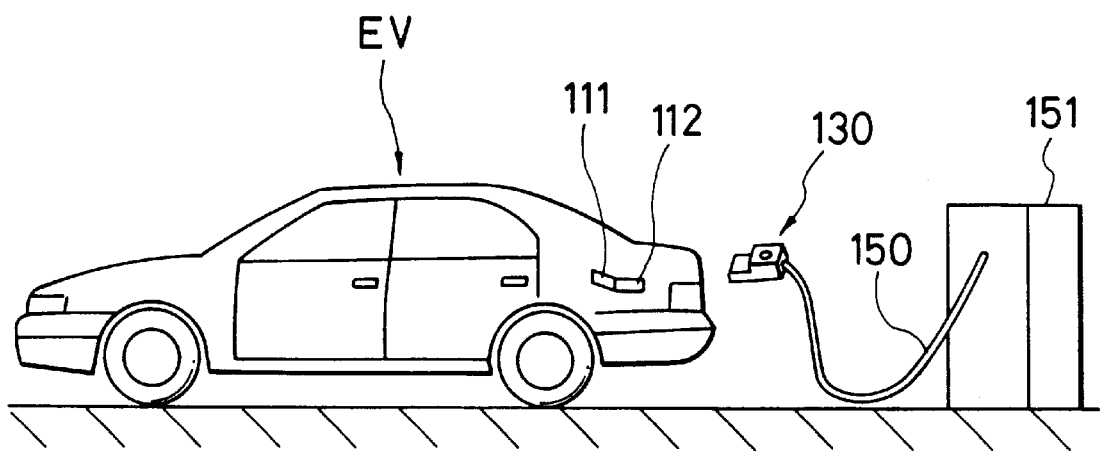
FIG. 23 is a schematic side view of the whole of a twelfth embodiment of a charging system according to the invention.

The general structure of the present charging system is as shown in FIG. 23. In particular, a receive portion 112 which can be opened and closed, for example, by a cover 111 is formed in the outside portion of the vehicle body of the electric vehicle EV, while a charging coupler 130 to be described later can be inserted into and set in the receive portion 112. To the charging coupler 130, there is connected a charging power cable 150 which is in turn connected to a power source device or charging unit 151 including a high-frequency power source 152 for outputting a high-frequency voltage of 100 kHz or the like.

Figure 24:
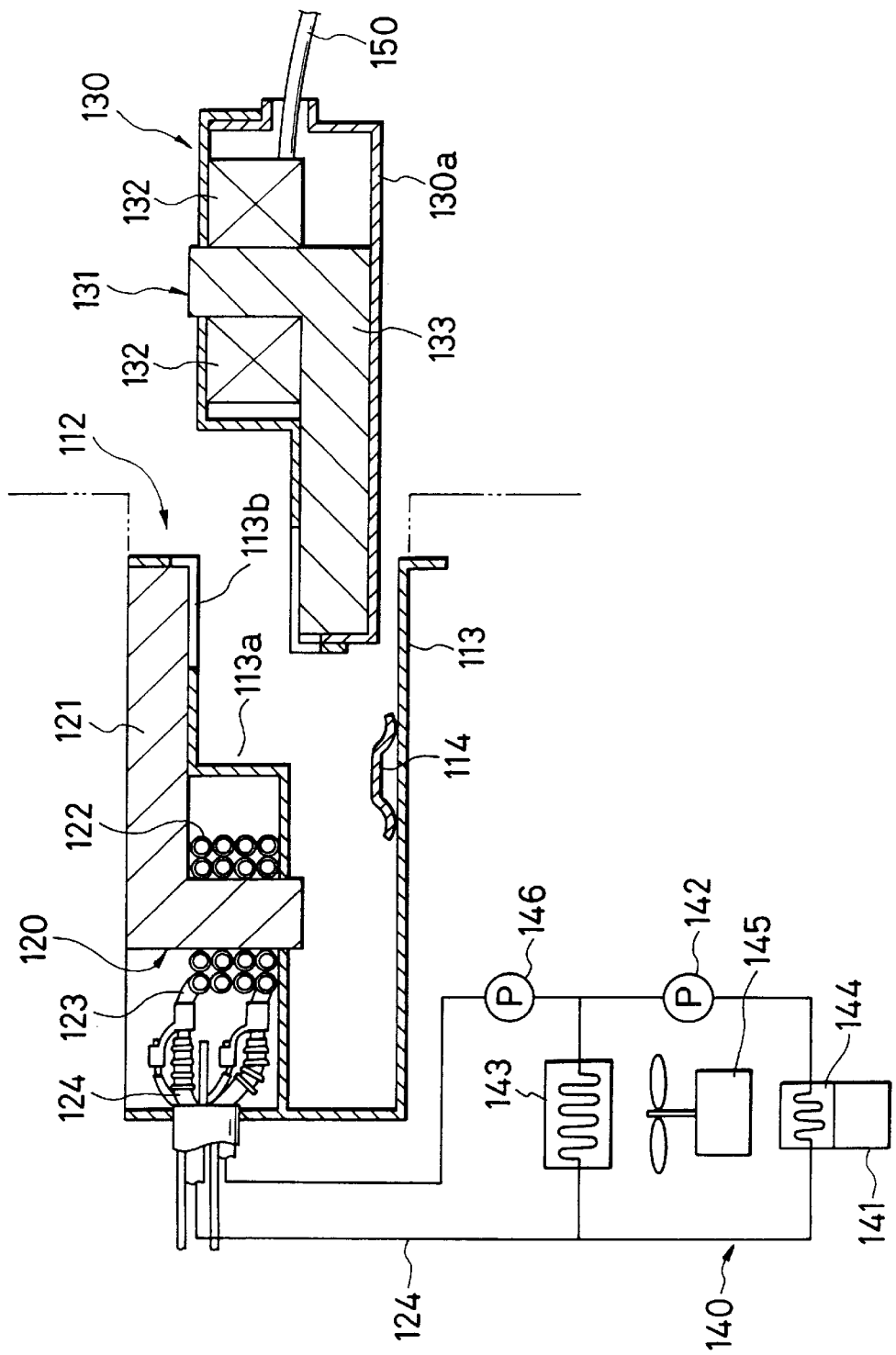
FIG. 24 is a longitudinal section view of primary and secondary coil units employed in the twelfth embodiment.

The charging coupler 130, as shown in FIG. 24, is structured in such a manner that a primary coil unit 131 is stored in a housing 130a, while the primary coil unit 131 is structured such that a primary coil 132 is wound around a primary core 133. The primary core 133 is formed of ferrite or the like and has such a shape that a quadrangular prism is bent into an L shape, while the primary core 133 is fixed to the interior portion of the housing 130a with the long side of the L shape thereof arranged sideways.

On the other hand, in the above-mentioned receive portion 112 of the electric vehicle EV, there is mounted a coupler receive case 113 which forms a recessed portion 113a opened outwardly, and a secondary coil unit 120 is arranged in the coupler receive case 113. The secondary coil unit 120 is structured in such a manner that a secondary coil 122 is wound around a secondary core 121 which is identical in shape with the above-mentioned primary core 133 and is formed of ferrite, and the output terminal of the secondary coil 122 is connected to a charging circuit for charging a power battery (not shown) which is the battery device of the electric vehicle EV, thereby being able to rectify a high-frequency electromotive force induced in the secondary coil 122 so as to charge the power battery. The secondary core 121 is fixed to the coupler receive case 113 with the long side of the L shape thereof arranged sideways, and the short side of the L shape thereof extends downwardly so that the lower end portion thereof extends through the coupler receive case 113 and projects slightly into the recessed portion 113a. Also, the leading end side of the long side of the L shape of the secondary core 121 extends through an opening 113b formed in the front end portion of the coupler receive case 113 and is exposed toward the interior portion of the recessed portion 113a. By the way, a plate spring 114 is mounted on the bottom portion of the recessed portion 113a of the coupler receive case 113. That is, when the charging coupler 130 is inserted into the recessed portion 113a, the plate spring 114 energizes the charging coupler 130 upwardly (that is, toward the secondary coil unit 120) to thereby bring the mutually opposed surfaces of the two cores 121 and 133 into contact with each other, so that a closed single-loop magnetic circuit can be completed by the two cores 121 and 133.

Now, the second coil unit 120 is structured by winding a conductive pipe 123 around the short side portion of the secondary core 121 two or more times. In the present embodiment, the conductive pipe 123 is formed of a copper alloy and, for example, the conductive pipe 123 has a diameter of 5 mm, a thickness of 0.5 mm, and an inside winding diameter of approx. 25 mm. Also, on the inner peripheral side of the secondary coil 122, that is, between the same and the secondary core 121, for example, there is applied a heat transferable silicone grease or the like. Due to this, the heat transfer property between the secondary core 121 and secondary coil 122 is enhanced when compared with a case where the silicone grease is not applied, so that the secondary coil 122 is wound around the secondary core 121 in a heat transferable manner. By the way, although not shown, enamel coatings or the like are applied onto the inside and outside surfaces of the conductive pipe 123 for the sake of insulation.

Figure 25:
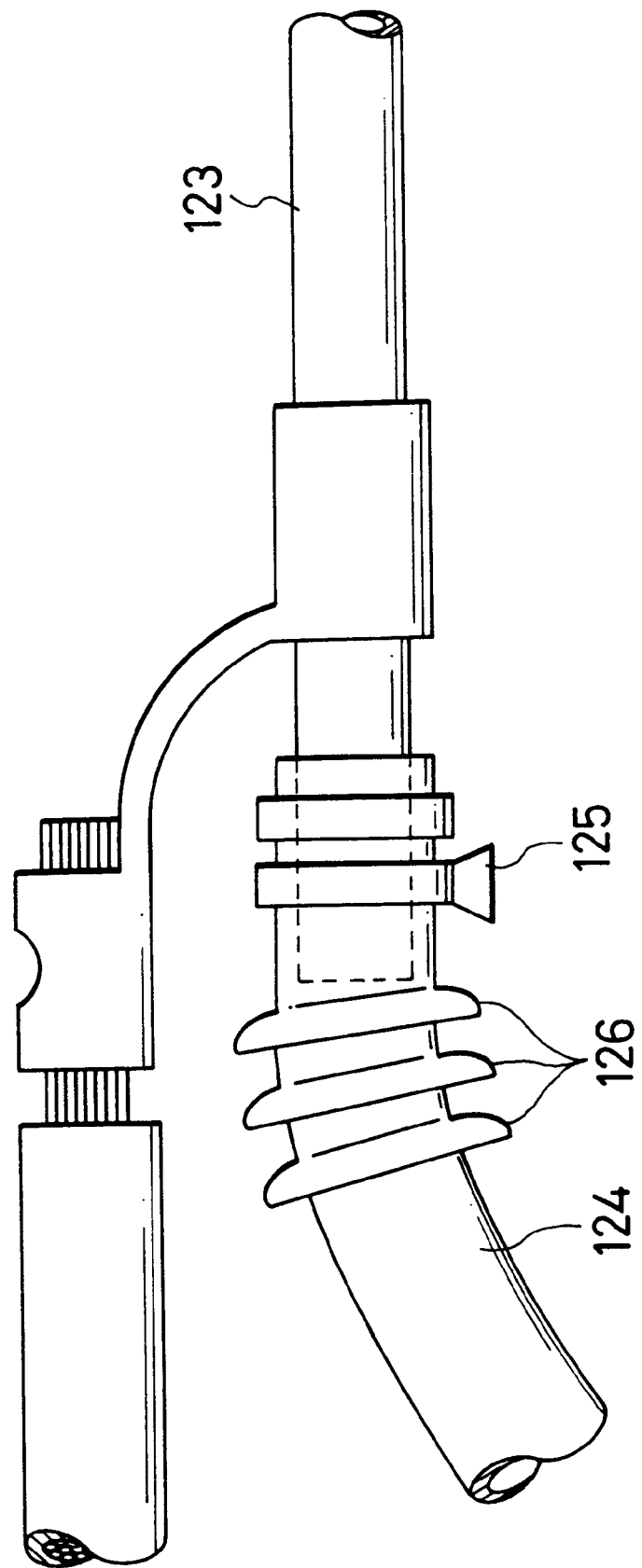
FIG. 25 is an enlarged side view of a connecting portion of a conductive pipe employed in the twelfth embodiment.

And, a connecting structure for connecting the secondary coil 122 with the power battery side is as shown in FIG. 25. That is, a refrigerant circulation pipe 124 is fitted with the end portion of the conductive pipe 123, while the refrigerant circulation pipe 124 is connected with the conductive pipe 123 by a pipe clamp 125 in a watertight manner. Also, a plurality of water drain shades 126 are formed integrally in the connecting end portion of the refrigerant circulation pipe 124. That is, even if water drops are caused to flow from the conductive pipe 123 side due to the condensation of the cooling water on the conductive pipe 123 or the like, or, on the contrary, even if water drops are caused to flow from the refrigerant circulation pipe 124, the water drain shades 126 prevent such water drops from flowing on the opposite side. These refrigerant circulation pipes 124, as shown in FIG. 24, are respectively connected in communication with the refrigerant circulating passage of a cooling device 140 which is used to cool an inverter device 141 or the like which is equipped inherently in the electric vehicle EV. The cooling device 140 is structured such that, by driving a circulation pump 142 for the inverter, the cooling water as a refrigerant can be circulated to a heat exchanger 144 provided in the inverter device 141; and also that the cooling water heated when it passes through the heat exchanger 144 can be cooled by a radiator device 143 to which the air is being applied by a fan device 145. And, in the radiator device 143, a cooling water circulating passage communicating with a charging circulation pump 146 and the above-mentioned secondary coil 122 in this order is formed in parallel to the above-mentioned refrigerant circulating passage of the inverter device 141. Thus, by operating the charging circulation pump 146, the cooling water is allowed to flow to the secondary coil 122 and radiator device 143 in this order through the refrigerant circulation pipe 124. By the way, the secondary coil 122 is arranged such that it allows the cooling water to flow from the inner peripheral side thereof toward the outer peripheral side thereof.

The present embodiment is structured in the above-mentioned manner and, now, description will be given below of the operation of the present structure. That is, to charge the electric vehicle EV, at first, the charging coupler 130 is inserted into the receive portion 112 of the vehicle body of the electric vehicle EV. In particular, the charging coupler 130 is inserted into the deepest portion of the receive case 113 and, within the coupler receive case 113, the charging coupler 130 is pressed against the secondary coil unit 120 side by the plate spring 114 to thereby bring the two cores 121 and 133 into engagement with each other, which completes a closed-loop magnetic circuit. At the then time, if a power switch (not shown) of the power source device 151 is switched on, then the high-frequency power source 152 is actuated to thereby apply a high-frequency voltage to the primary coil 132 through the charging power cable 150. Responsive to this, the primary coil 132 is excited, which in turn causes the secondary coil 122 to generate an electromotive force therein, thereby being able to charge the power battery of the electric vehicle EV.

In such charging process, both of the primary coil unit 131 and secondary coil unit 120 generate heat. However, in the electric vehicle EV, since the cooling device 140 incorporated in the electric vehicle EV is actuated and the charging circulation pump 146 is thereby operated, there is provided a refrigerant circulation flow in which the cooling water flows within the conductive pipe 123 through the refrigerant circulation pipe 124 and the cooling water is returned from the radiator device 143 to the charging circulation pump 146 again through the return passage side refrigerant circulation pipe 124. Due to this, the heat generated in the conductive pipe 123 is transferred immediately to the cooling water flowing through the interior portion of the conductive pipe 123 and is carried to the cooling device 140 side, where the thus heated cooling water is cooled by the fan device 145 and is circulated again. That is, the conductive pipe 123 can be cooled immediately in spite of the situation that it generates a large amount of Joule heat during the charging operation, thereby being sure to prevent the secondary coil 120 from rising in temperature greatly. On the other hand, the heat generated in the primary coil unit 131, due to the fact the primary and secondary cores 133 and 121 are in engagement with each other, is transferred through the primary core 131 to the secondary core 121, where the heat is cooled.

As has been described hereinbefore, according to the present embodiment, there can be obtained the following effects.

(1) Since the secondary coil unit 120 can be cooled by use of the cooling device 140 inherently provided in the electric vehicle EV, the cooling operation of the present charging system can be executed with no need for provision of a special cooling device for the present charging system. Realization of such cooling means that the whole charging system can be made compact or can be made large in capacity.

(2) Due to the fact that the secondary coil 122 is formed of a conductive pipe and the cooling water is allowed to flow through the interior portion of the conductive pipe, the coil conductor itself, which is a source of generation of Joule heat, is cooled from the inside thereof as well as the surface of the secondary core 121, which is a source of generation of hysteresis loss, can be cooled directly, thereby being able to realize very highly efficient cooling.

By the way, in the present embodiment, the charging power source 151 is set such that it outputs a high frequency of 100 kHz, and a current depth due to the skin effect of a secondary current flowing through the secondary coil 122 is computed as approx. 0.3 mm from the surface of the secondary coil 122. For this reason, even if the coil conductor is hollow, there is no possibility that the electric resistance thereof can increase, that is, the hollow structure of the coil conductor does not give rise to the lowered efficiency or generation of heat. Or rather, the hollow structure can be used cleverly to realize effective cooling.

(3) Application of the silicone grease to the gap between the secondary coil 122 and secondary core 121 allows the secondary coil 122 to be wound around the secondary core 121 in a heat transferable manner. Thanks to this, the heat generated in the secondary core 121 can also be transferred to the conductive pipe 123 smoothly and can be cooled here, which makes it possible to restrict an increase in the temperature of the secondary core 121 effectively.

(4) Since the cooling water is allowed to flow from the inner peripheral side of the secondary coil 122 toward the outer peripheral side thereof, the whole of the charging system can be cooled efficiently and uniformly in spite of the situation that the inner peripheral side of the secondary coil 122 is near to the secondary core 121 and is thus easy to rise in temperature.

Thirteenth Embodiment

Figure 26:
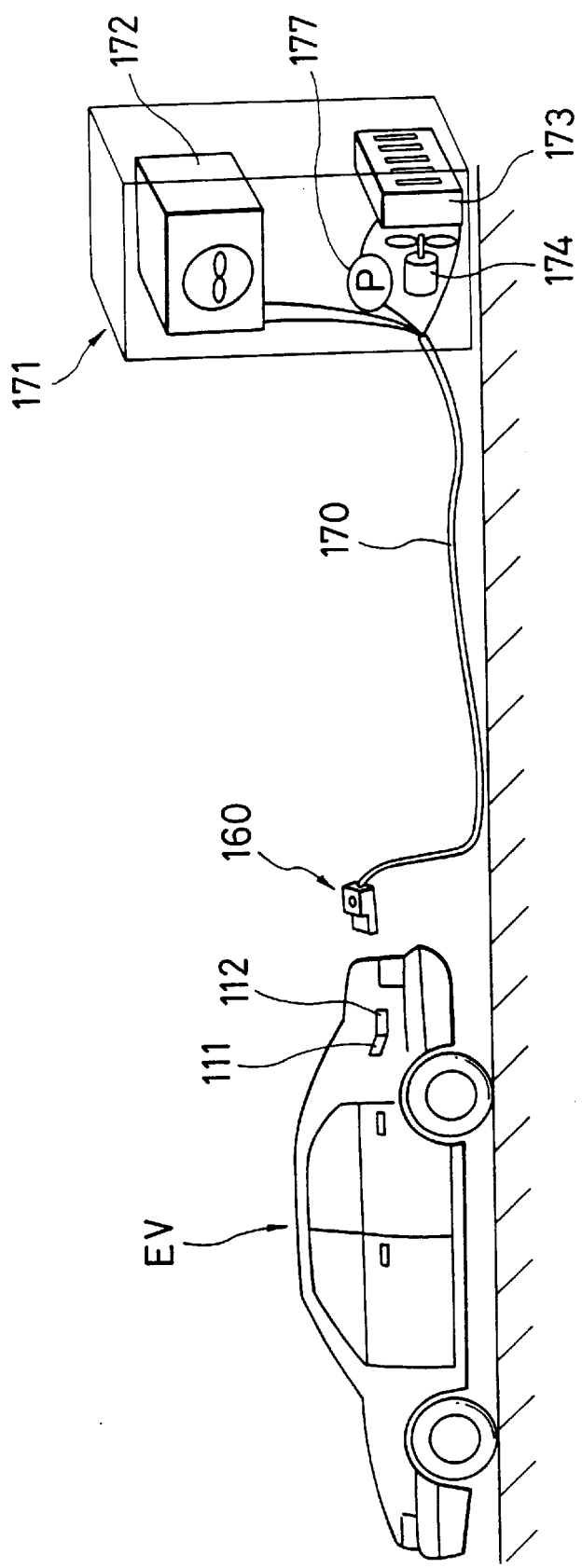
FIG. 26 is a schematic side view of the whole of a thirteenth embodiment of a charging system according to the invention.
Figure 27:
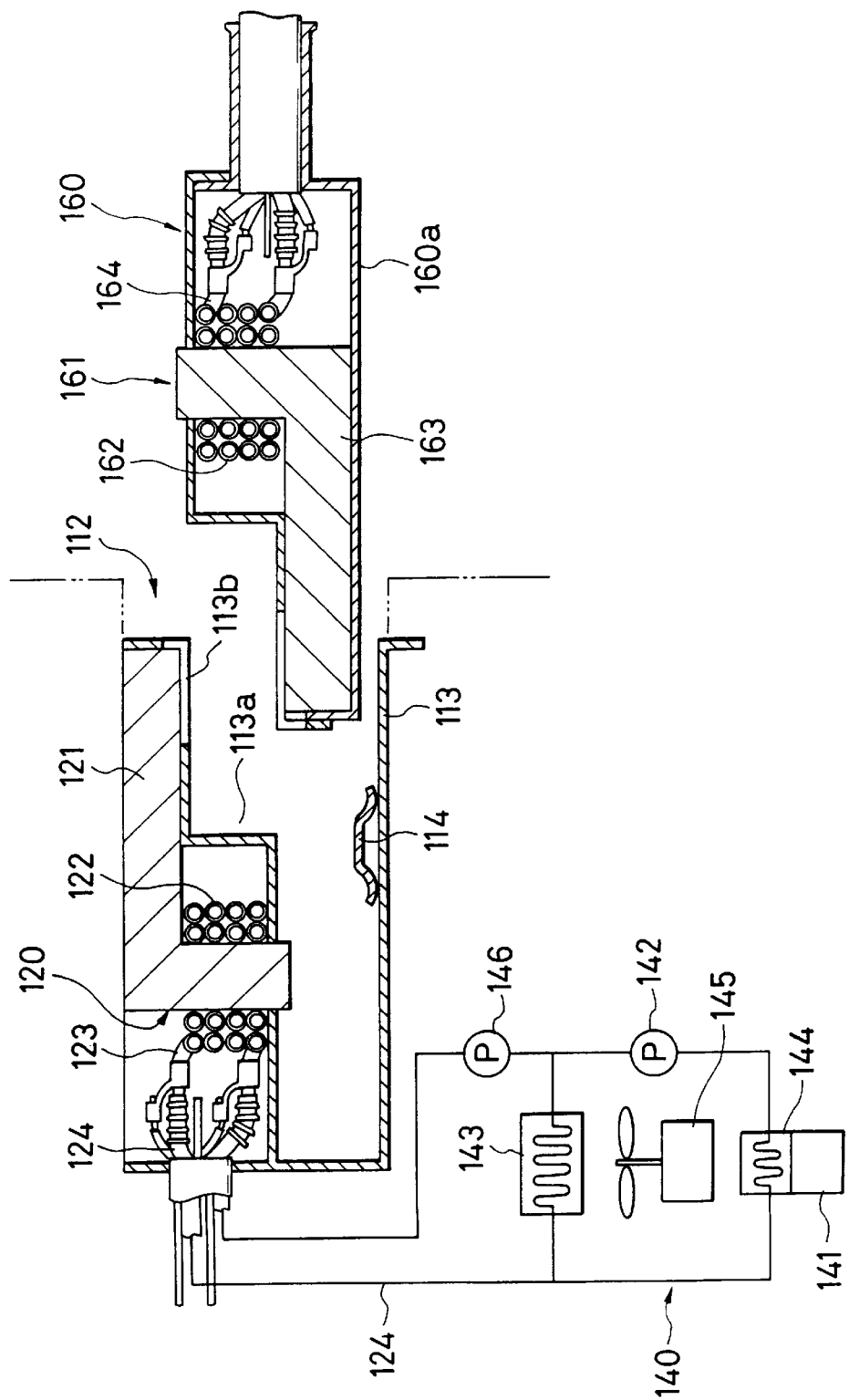
FIG. 27 is a longitudinal section view of primary and secondary coil units employed in the thirteenth embodiment.
Figure 28:
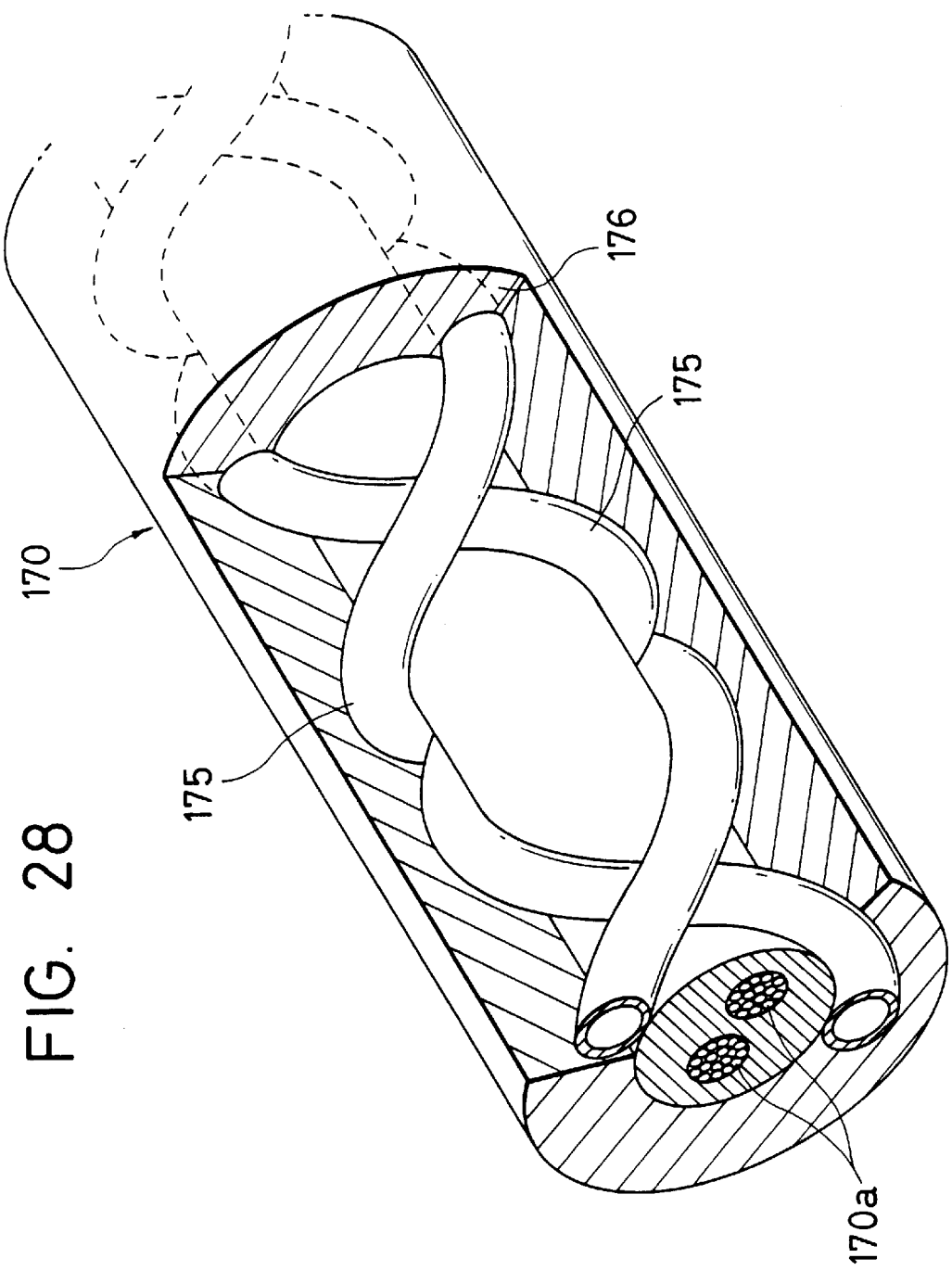
FIG. 28 is a partially broken perspective view of a charging power cable employed in the thirteenth embodiment.

Now, FIGS. 26 to 28 show a thirteenth embodiment of a charging system according to the invention, in which the primary coil unit side is also cooled by means of circulation of a refrigerant.

The whole structure of the present charging system is as shown in FIG. 26, in which a receive portion 112 openable and closable by a cover 111 or the like is formed in the outside portion of the vehicle body of the electric vehicle EV and a charging coupler 160 to be described later can be inserted into and set in the receive portion 112 of the vehicle body of the electric vehicle EV. To the charging coupler 160, there is connected a charging power cable 170 which is in turn connected to a power source unit 171. In the power source unit 171, there are provided a high-frequency power source 172 used to output a high-frequency voltage of 100 kHz or the like, as well as an air-cooling type of radiator device 173 for radiating the heat of cooling water serving as a refrigerant to be described later and an air cooling fan 174 for air cooling the radiator device 173.

Similarly to the first embodiment, in the receive portion 112 of the electric vehicle EV, there is mounted a coupler receive case 113 forming a recessed portion 113a which is open toward the outside, and a secondary coil unit 120 is disposed in the coupler receive case 113. The secondary coil unit 120 is structured such that a secondary coil 122 formed of a conductive pipe 123 is wound around a secondary core 121 which is formed of ferrite; and, a refrigerant, which is contained in a cooling device 148 and is used to cool an inverter device 141 or the like inherently provided in the electric vehicle EV, is allowed to flow through the interior portion of the secondary coil 122. The output terminal of the secondary coil 122 is connected to a charging circuit used to charge a power battery (not shown) which is a power storage device of the electric vehicle EV, so that a high-frequency electromotive force induced in the secondary coil 122 can be rectified to thereby charge the power battery.

On the other hand, the charging couple 160 is structured such that a primary coil unit 161 is stored in a housing 160a, while the primary coil unit 161, differently from the twelfth embodiment, is structured such that a primary coil 162 formed of a similar conductive pipe 164 to that of the secondary coil 122 is wound around a primary core 163. The primary core 163 is similar to the primary core employed in the twelfth embodiment and, referring to the primary coil 162, similarly to the secondary coil 122, with a heat transferable silicone grease or the like applied between the primary coil 162 and primary core 163, the primary coil 162 is wound around the primary core 163 in a heat transferable manner. By the way, although not shown, an enamel coating or the like is applied onto the inner and outer surfaces of the conductive pipe 164 of the primary coil 162 to thereby insulate the same surfaces.

Also, as shown in FIG. 28, the above-mentioned charging power cable 170 includes two core wires 170a; two refrigerant circulation pipes 175 respectively forming a forward passage side and a backward or return passage side of the refrigerant circulation passage are wound around the outer peripheral side of the two core wires 170a through insulation layers in the mutually reversed spiral shapes; and, an outer cover layer 176 is applied to the outer periphery of the thus wound refrigerant circulation pipes, thereby uniting the whole of the charging power cable 170 as an integral body. By the way, each of the refrigerant circulation pipes 42 is formed of heat resisting and flexible synthetic resin such as silicone resin or the like. And, the two core wires 170a of the charging power cable 170, on the power source device 171 side, are respectively connected to the output lines of the high-frequency power source 172; and, the forward passage side refrigerant circulation pipe 175 is coupled to a circulating pump 177 provided within the power source device 171, while the return passage side refrigerant supply pipe 175 is coupled to the radiator device 173. By the way, a connecting structure for connecting the primary coil 162 to the charging power cable 170 is similar to that shown in FIG. 25.

The present embodiment is structured in the above-mentioned manner and, now, description will be given below of the operation of the present structure. That is, to charge the electric vehicle EV, at first, the charging coupler 160 is inserted into the receive portion 112 of the vehicle body. In particular, the charging coupler 160 is inserted into the deepest portion of the receive case 113 and, within the coupler receive case 113, the charging coupler 160 is pressed against the secondary coil unit 120 side thereof by the plate spring 114 to bring the two cores 121 and 163 into engagement with each other, thereby completing a closed-loop magnetic circuit. At the then time, if a power switch (not shown) of the power source device 171 is switched on, then not only the circulation pump 177 and air cooling fan 174 are actuated but also the high-frequency power source 172 is operated to thereby apply a high-frequency voltage to the primary coil 162 through the charging power cable 170. Responsive to this, the primary coil 162 is excited, which in turn causes the secondary coil 122 to generate an electromotive force therein, thereby being able to charge the power battery of the electric vehicle EV.

On the other hand, since the circulation pump 177 of the power source device 171 is in operation simultaneously with the above charging operation, there is generated a cooling water circulation flow in which the cooling water flows within the conductive pipe 164 through the forward passage side refrigerant circulation pipe 175 of the charging power cable 170 and the cooling water is returned again from the radiator device 173 to the circulation pump 177 through the return passage side refrigerant circulation pipe 175. Due to this, the heat generated in the primary coil unit 161 is transferred immediately to the cooling water flowing through the interior portion of the primary coil 162 and is thus carried to the radiator device 173 side, where the cooling water is cooled by the air cooling fan 174 so that it can be circulated again. That is, since the heat generated in the primary coil unit 161 can also be cooled immediately by the cooling water flowing through the interior portion of the primary coil 162, it is sure to prevent the primary coil unit 161 from rising in temperature greatly. Also, the secondary coil unit 120, similarly to the first embodiment, can be cooled by the cooling device 140 which is provided in the electric vehicle EV.

According to the present embodiment, as the primary coil unit 161 is cooled by the radiator device 173 which is provided on the power source device 171 side, the cooling device 140 provided on the electric vehicle EV may cool only the secondary coil unit 120, so that the thermal load of the cooling device 140 can be reduced advantageously. By the way, although the primary coil unit 161 is also cooled by the cooling water in this manner, the refrigerant circulation pipes 175 are wound around the outer periphery of the core wires 170a to be thereby united with the charging cable 170, which not only makes it possible to cool the core wires 170a as well but also allows the charging and cooling operations to be carried out simply by handling a single cable or the charging power cable 170, thereby being able to simplify the charging operation. Also, because the radiator device 173 is incorporated in the power source device or charging unit 171, the whole charging facilities can be made compact. Further, since the cooling water is allowed to circulate while it is being cooled by the radiator device 173, there is eliminated the wasteful use of the refrigerant, that is, the refrigerant or the cooling water can be used economically.

Fourteenth Embodiment

Figure 29:
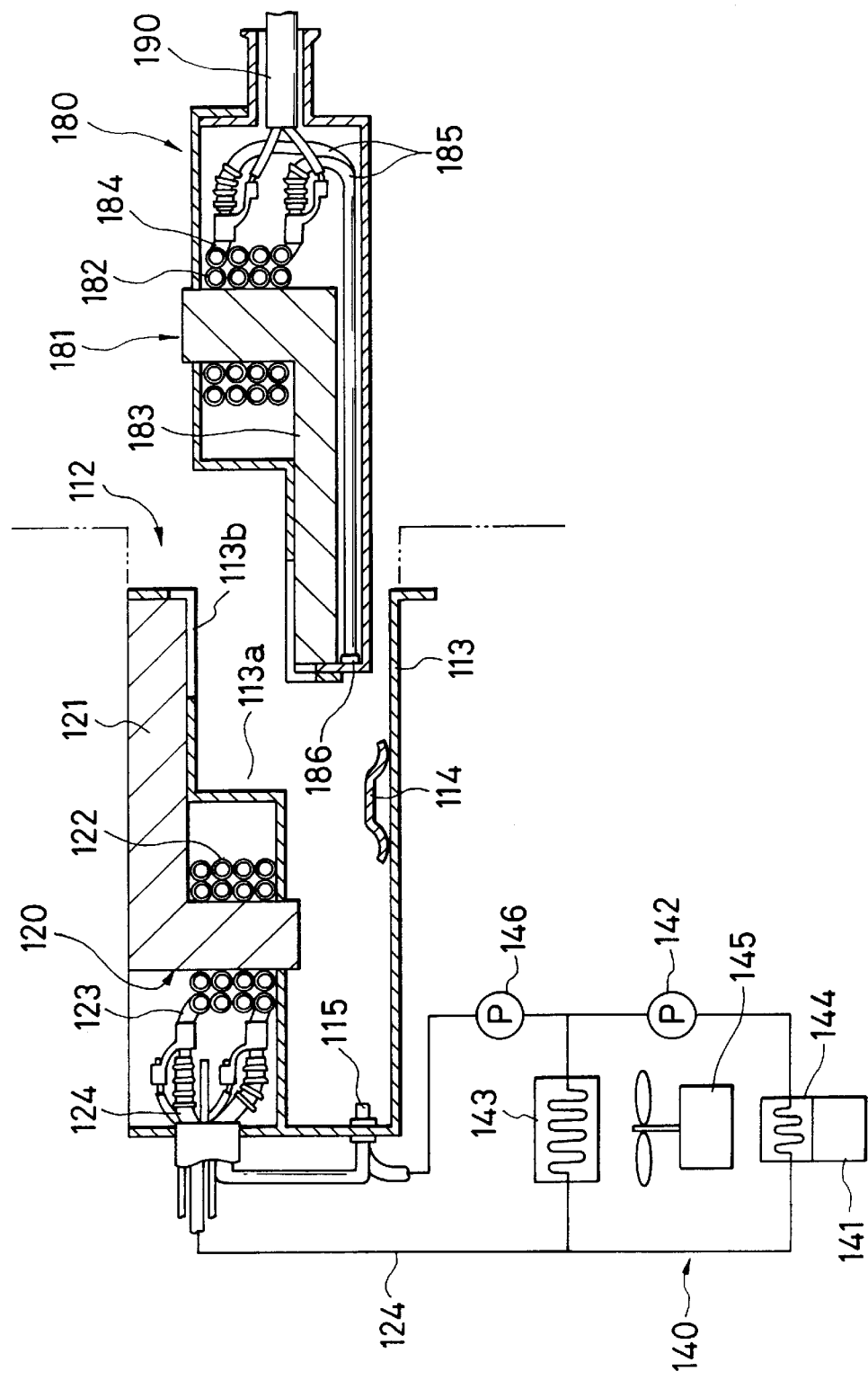
FIG. 29 is a longitudinal section view of primary and secondary coil units employed in a fourteenth embodiment of a charging system according to the invention.

Now, FIG. 29 shows a fourteenth embodiment of a charging system according to the invention, in which a cooling structure for cooling the primary coil unit is improved. Since the secondary side structure of the present embodiment is similar to the twelfth embodiment, the same parts are given the same designations and thus the duplicate description thereof is omitted here.

In particular, a primary coil unit 181, similarly to the thirteenth embodiment, is structured such that a conductive pipe 184 is wound around a primary core 183, while cooling water is allowed to flow through the interior portion of the conductive pipe 184. To the two ends of the conductive pipe 184, there are connected two connecting pipes 185 which are respectively connected to two female-type joints 186 (in FIG. 29, only one of them is shown) provided on the leading end portion of a charging coupler 180. On the other hand, a coupler receive case 113 includes on the deep wall thereof two male-type joints 115 (in FIG. 29, only one of them is shown) to which are connected not only the return passage side one of the refrigerant circulation pipes 124 of a secondary coil 122 but also a pipe that is connected in communication with an inverter circulation pump 142 of a cooling device 140. The male-type joints 115 respectively correspond to the female-type joints 186 mounted on the leading end portion of the charging coupler 180, that is, if the charging coupler 180 is inserted into the coupler receive case 113, the male- and female-type joints are connected with each other to thereby form a liquid passage. When the two kinds of joints 115 and 186 are not connected with each other, valve mechanisms respectively incorporated therein are closed to thereby prevent the liquid from flowing out from the joints. By the way, a primary coil 182 can receive high-frequency power from the power source device through a charging power cable 190.

With use of the above structure, if the charging coupler 180 is set in the receive portion 112 of the electric vehicle EV, then, as described above in connection with the twelfth embodiment, not only the magnetic circuit is completed by the respective cores 121 and 183 but also the joints 115 and 186 are connected with each other, thereby forming a cooling water passage toward the primary coil unit 181 side. As a result of this, the charging circulation pump 146 of the cooling device 140 is actuated, so that the cooling water flows not only through the secondary coil unit 120 but also through the primary coil 182 of the primary coil unit 181 to thereby cool the primary coil unit 181 side as well.

Therefore, according to the present embodiment, in particular, there is obtained an effect that, even if a special cooling device is not provided on the power source device side or on the charging unit side, the primary coil unit 181 side can also be cooled by use of the cooling device 140 which is provided in the electric vehicle EV.

Fifteenth Embodiment

Figure 30:
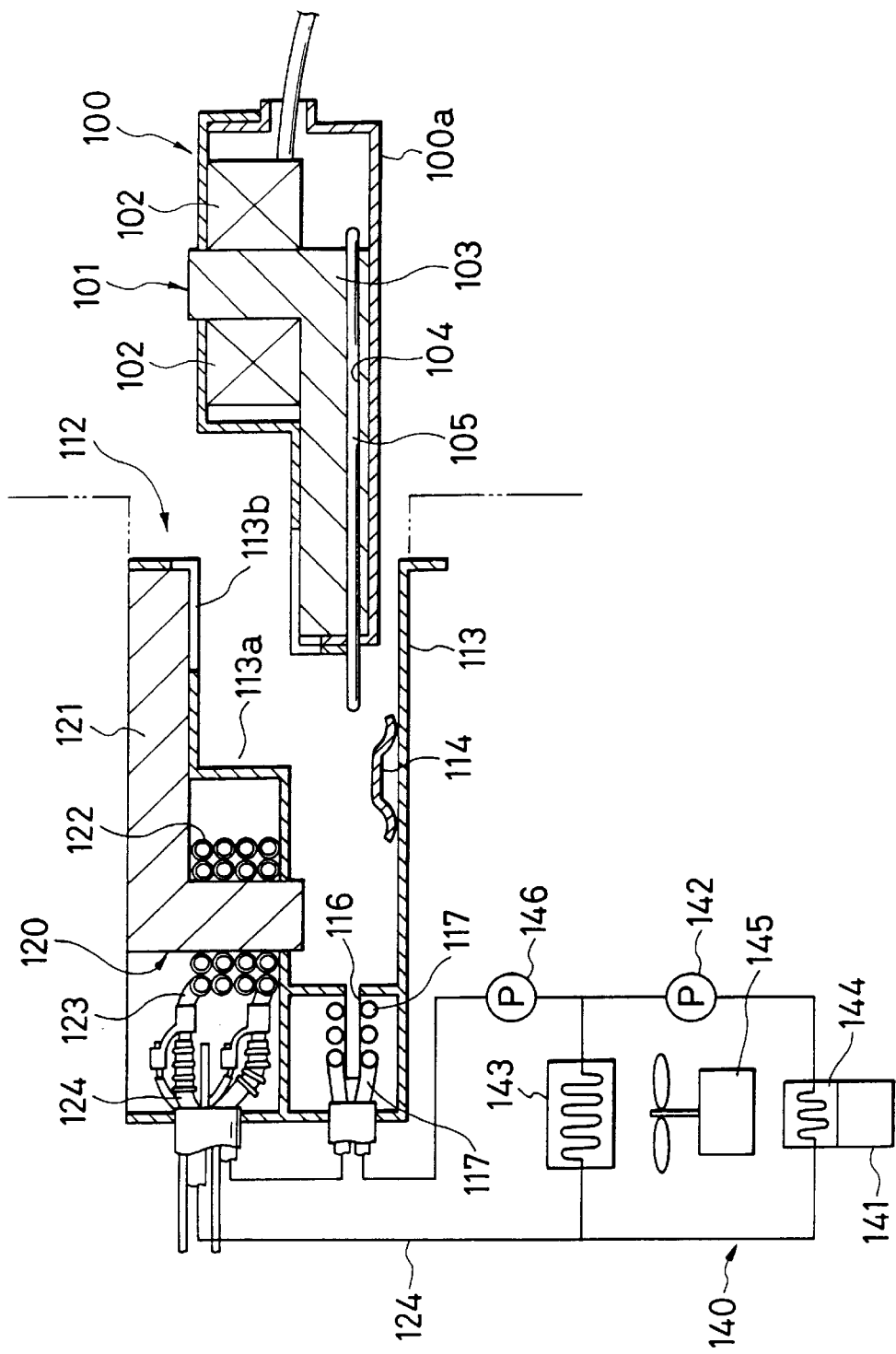
FIG. 30 is a longitudinal section view of primary and secondary coil units employed in a fifteenth embodiment of a charging system according to the invention.
Figure 31:
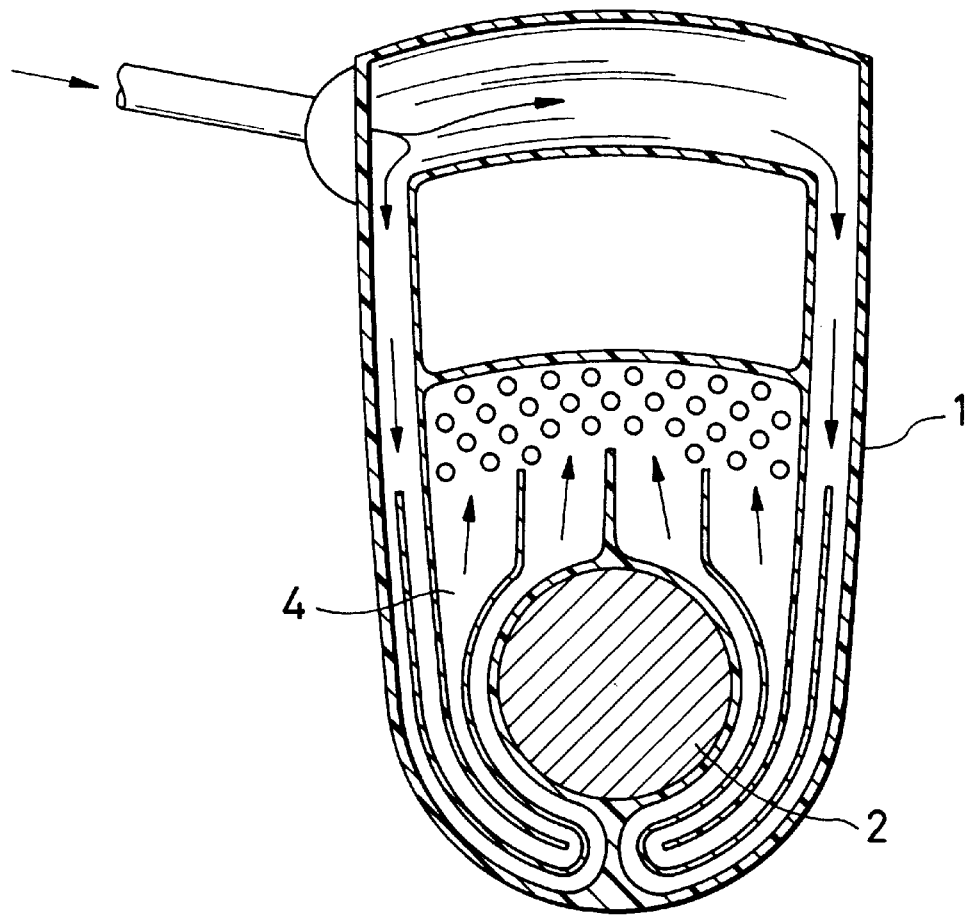
FIG. 31 is a section view of a charging coupler employed in a conventional charging system; and, FIG. 32 is an enlarged section view of the charging coupler employed in the conventional charging system.
Figure 32:
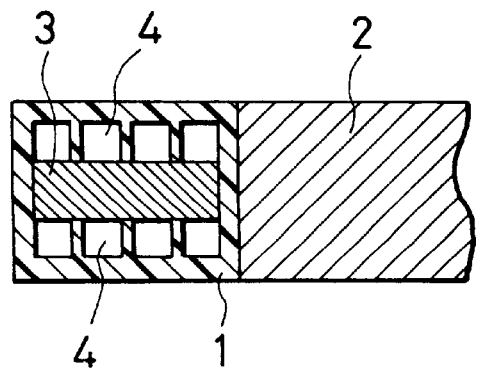

Now, FIG. 30 shows a fifteenth embodiment of a charging system according to the invention which is different from the first embodiment in that a structure for cooling the primary coil unit thereof is improved.

In particular, similarly to the twelfth embodiment, the present primary coil unit 101 is structured such that a primary coil 102 formed of Litz wires is wound around a primary core 103 which is formed of ferrite in an L-like shape; and, in the long side portion of the primary core 103, there is formed a through hole 104 which extends in the longitudinal direction thereof, while a heat pipe 105 equivalent to a heat transferable member is arranged in the through hole 104 in such a manner that it extends through the through hole 104. The leading end of the heat pipe 105 projects out from the leading end of a housing 100a forming a charging coupler 100. On the other hand, on the receive portion 112 side, a heat pipe storage cylinder 116 is provided in the deep wall of the coupler receive case 113 and thus, if the charging coupler 100 is set in the receive portion 112, then the exposed end of the heat pipe 105 is inserted into the heat pipe receive cylinder 116. And, a cooling pipe 117 is wound around the outer periphery of the heat pipe receive cylinder 116, while the cooling pipe 117 is connected to a refrigerant circulation pipe 124 which is in turn connected to a secondary coil 122.

In such structure, the heat of the primary coil unit 101 is transferred to the heat pipe 105, thereby causing the heat pipe receive cylinder 116 to rise in temperature. On the other hand, since the heat pipe receive cylinder 116 is cooled by the cooling water of the cooling device 140 flowing through the cooling pipe 117, the heat generated in the primary coil unit 101 is cooled by the cooling device 140 in the end. Therefore, according to the present structure, similarly to the previously described second and third embodiments, the primary coil unit 101 can be cooled effectively. Also, there is eliminated the need for provision of not only the primary side cooling device as in the second embodiment but also the passage joints as in the third embodiment, which makes it possible to simplify the structure further.

Other Embodiments

There have been illustrated various embodiments of a charging system according to the invention hereinbefore by means of the foregoing description and the accompanying drawings. However, the invention is not limited to these illustrated embodiments but, for example, the following embodiments also fall within the technical scope of the invention and further, in addition to the following embodiments, various changes and modifications are also possible without departing from the subject matter of the invention.

(1) In the above-mentioned respective embodiments, the liquid refrigerant is allowed to circulate through the interior portion of the conductive pipe. However, this is not limitative but, for example, it is also possible to employ a cooling structure of a heat pipe type. That is, to realize this structure, a conductive pipe forming a primary coil may be connected to a radiator device provided at a position to be cooled by the open air by means of a refrigerant pipe and, at the same time, the interior portion of the conductive pipe may be filled up with a refrigerant which vaporizes at a relatively low temperature. With use of this structure, within the primary coil, the refrigerant is vaporized due to the coil heat, the vaporized refrigerant flows to the radiator device where it is cooled and is thereby liquefied, and the thus liquefied refrigerant circulates back again to the primary coil, whereby the primary coil can be cooled efficiently.

(2) In the above-mentioned respective embodiments, as the conductive pipe, there is used a conductive pipe which has a circular section. However, this is not limitative but it is also possible to use a conductive pipe which has a square-shaped section. In this case, since a coil formed of such conductive pipe can be wound tightly around a primary side core, the heat transfer property of the coil with respect to the core is enhanced to thereby be able to improve the cooling property of the core.

(3) In the above-mentioned respective embodiments, the refrigerant is allowed to flow through the interior portion of the conductive pipe. However, the invention is not limited to this but the refrigerant may also be made to flow not only inside but also outside the conductive pipe to thereby cool the coil and core.

(4) The manner of winding of the conductive pipe is not limited to the two layer winding as in the above-mentioned respective embodiments but one layer winding or three or more layer winding is also possible. In particular, with use of one layer winding, the heat transfer property of the conductive pipe with respect to its associated core is enhanced to thereby be able to contribute to the cooling of the core. Also, with use of three or more layer winding, heat transferable material can be filled into between the winding layers, so that the heat can be transferred effectively.

(5) Now, when using a water-system refrigerant, as anti-freezing measures to protect the water-system refrigerant against freezing when it is used in cold districts or in winter, the followings are applicable:
 i) An antifreeze solution is mixed into the refrigerant.
 ii) When the charging operation is completed, the cooling water is drained automatically. In this case, for further positive drainage, compressed air may be fed into the passage of the cooling water after the cooling water is drained.
 iii) An antifreeze valve is provided in the passage of the cooling water so that, if the temperature falls down to a level where the cooling water is freezable, then the cooling water can be drained automatically.
 iv) A heater is provided in the passage of the cooling water so that, if the temperature falls down to a level where the cooling water is freezable, the heater is energized to thereby heat the cooling water.

(6) In the above-mentioned fourth embodiment, the bobbin 60 is structured as an integral cylindrical body. However, this is not limitative but the bobbin may also be structured by combining together a plurality of spacers respectively extending in the axial direction of the primary coil 32. Especially, with use of a structure that the bobbin is divided to a plurality of spacers respectively extending in the axial direction of the primary coil, even when the bobbin is formed of conductive metal, an eddy current is hard to occur. That is, with use of such structure, not only the eddy current can be restricted but also the heat transfer property can be enhanced, thereby being able to further enhance the cooling property of the core.

(7) A fin for cooling may be provided in the primary side core or secondary side core. In this case, the cooling fin may be formed of the same material as the core in such a manner that the fin and core are united together into an integral body. Or, a metal fin, which is formed of highly heat transmissive material such as aluminum or the like, may be mounted on the core in an insulated manner.

In the above-mentioned respective embodiments, the primary and secondary coils are respectively formed of conductive pipes and the refrigerant is allowed to flow through the interior portions of the conductive pipes. However, the invention is not limited to this but it is also possible to employ another structure in which the coils are formed of Litz wires or the like and a refrigerant passage is formed in the primary and secondary cores, thereby cooling the cores. The essential thing is that the desired object can be achieved by cooling the primary or secondary coil unit by use of a cooling device provided in the electric vehicle.

In the above-mentioned respective embodiments, water is used as the refrigerant but this is not limitative. For example, a low-temperature air (including the open air) may be fed into the refrigerant passage to thereby cool the coils and cores. Also, even when a liquid refrigerant is used, of course, not only water but also various kinds of oils, and hydrocarbon-system solvents such as flon or the like can also be used as a refrigerant.

In the above-mentioned respective embodiments, as radiating means, a radiator device is provided in the interior portion of a power source device or a charging unit. However, this is not limitative but, for example, when a refrigerant supply passage is formed integrally with a power cable and also when it can be expected that the heat of the refrigerant can be radiated through the power cable, the power cable can also be used as radiating means.

The refrigerant supply passage may not always be formed integrally with the power cable, but it may be structured separately from the power cable, that is, it may be structured as a hose which is exclusively used to supply the refrigerant.

What is claimed is:

1. A charging system for use with an electric vehicle comprising:
 a primary coil which is excited to thereby generate an electromotive force in a secondary coil;
 said secondary coil electromagnetically connected to the primary coil; and
 a power battery device provided in said electric vehicle, said power battery being charged by the electromotive force generated in said secondary coil;
 wherein at least one of said primary coil and secondary coil is formed of a conductive pipe and a refrigerant is allowed to flow through the interior portion of said conductive pipe to thereby cool said coil.

2. A charging system as claimed in claim 1, wherein said conductive pipe is wound around a core in a heat transferable manner, and said coil and core are cooled by means of a refrigerant which is allowed to flow through the interior portion of said conductive pipe.

3. A charging system as claimed in claim 2, wherein said primary coil is formed of the conductive pipe and the refrigerant flows therethrough said, primary coil being wound around said primary side core in two or more layers, and said refrigerant is allowed to flow from the inner peripheral side of said primary coil toward the outer peripheral side thereof.

4. A charging system as claimed in claim 1, wherein at least one of projecting portion and a recessed portion is formed in the inner surface of said conductive pipe.

5. A charging system as claimed in claim 1, wherein both of said primary coil and said secondary coil are formed by of a conductive pipe and said refrigerant is allowed to flow to thereby cool said primary coil and said second coil.

6. A charging system as claimed in claim 1, wherein an insulation layer is formed inside of said conductive pipe and said refrigerant is a water-system refrigerant.

7. A charging system as claimed in claim 1, wherein a plurality of refrigerant discharge holes are formed in the peripheral surface of said conductive pipe.

8. A charging system as claimed in claim 7, wherein a passage space for allowing said refrigerant discharged from said refrigerant discharge holes to flow therethrough is provided between said primary side or secondary side core and coil.

9. A charging system for use with an electric vehicle comprising:
 a power battery device equipped in the electric vehicle which is charged by an electromotive force induced in a secondary coil provided in the electric vehicle;

a high-frequency power source device for charging;

a housing which is placeable in a receive portion formed in the portion of said electric vehicle in which said secondary coil is provided;

a primary side core which, if it is stored in said housing and is thus set in said receive portion together with said housing, can be connected with the secondary side core of said secondary coil to thereby complete a magnetic circuit;

a primary coil formed of a conductive pipe and wound around said primary side core in a heat transferable manner;

a charging power cable interposed between said high-frequency power source device and a connector case for allowing a high-frequency current to flow from said high-frequency power source device to said primary coil;

a refrigerant supply pipe so provided as to extend along said charging power cable for allowing a refrigerant to flow into said conductive pipe;

a radiator device provided in connection with said refrigerant supply pipe for radiating the heat of said refrigerant after which is heated because the refrigerant has cooled said primary coil and said primary side core; and a circulation pump actuatable in combination with said charging operation for returning said refrigerant cooled in said radiator device to said primary coil side through said refrigerant supply pipe to thereby circulate said refrigerant.

10. A charging system as claimed in claim 9, wherein said primary coil is wound around said primary side core in two or more layers, and said refrigerant is allowed to flow from the inner peripheral side of said primary coil toward the outer peripheral side thereof.

11. A charging system as claimed in claim 9, wherein at least one of projecting portion and a recessed portion is formed in the inner surface of said conductive pipe.

12. A charging system as claimed in claim 9, wherein said secondary coil on said electric vehicle side is also formed of a conductive pipe and a refrigerant from said refrigerant supply pipe is allowed to flow to thereby cool said second coil.

13. A charging system as claimed in claim 9, wherein an insulation layer is formed inside of said conductive pipe and said refrigerant is a water-system refrigerant.

14. A charging system as claimed in claim 9, wherein a plurality of refrigerant discharge holes are formed in the peripheral surface of said conductive pipe.

15. A charging system as claimed in claim 14, wherein a passage space for allowing said refrigerant discharged from said refrigerant discharge holes to flow therethrough is provided between said primary side or secondary side core and coil.

16. A charging system for use with an electric vehicle comprising:

a charging coupler which is to be mounted into a receive portion provided in the electric vehicle;

a primary coil built in the charging coupler which is excited by a charging power source to thereby generate an electromotive force in a secondary coil provided on the receive portion;

a battery device provided in the electric vehicle which is charged by the electromotive force generated in the secondary coil;

a refrigerant circulation passage for allowing a refrigerant to circulate through said charging coupler; and a radiator that discharges heat from the refrigerant flowing through said refrigerant circulation passage;

wherein said charging coupler is cooled by the circulation of said refrigerant, and wherein said primary coil of said charging coupler is formed of a conductive pipe, and said conductive pipe is formed as part of said refrigerant circulation passage so that said refrigerant is allowed to flow through said conductive pipe as well.

17. A charging system as claimed in claim 16, wherein a refrigerant circulation tube forming a part of said refrigerant circulation passage is formed integrally with a power cable for supplying power to said primary coil of said charging coupler.

18. A charging system as claimed in claim 16, wherein said radiator is incorporated integrally in said charging power source device.

19. A charging system for use with an electric vehicle comprising:

a primary coil unit provided in a charging coupler;

a charging power source for exciting said primary coil unit;

a secondary coil unit provided in said electric vehicle which is electromagnetically coupled with said primary coil unit, to thereby generate an electromotive force;

a battery device provided in the electric vehicle which is charged by the electromotive force generated in said secondary coil unit;

a primary refrigerant passage provided in said primary coil unit for cooling said primary coil unit;

a secondary refrigerant passage provided in said secondary coil unit for cooling said secondary coil units; and passage joints for connecting said primary and secondary refrigerant passages to each other.

20. A charging system as claimed in claim 19, wherein said passage joints are respectively disposed opposed not only to said charging coupler but also to a receive portion formed in said electric vehicle for receiving said charging coupler, and said passage joints is connectable with each other when said charging coupler is mounted into said receive portion to thereby bring said primary and secondary side refrigerant passages into communication with each other.

21. A charging system as claimed in claim 19, wherein each of said respective passage joints includes at least one valve mechanism therein which is arranged so as to close said refrigerant passages when the refrigerant passages are not connected with each other.

22. A charging system as claimed in claim 19, wherein at least one of said primary coil and secondary coil is formed of a conductive pipe and said primary side or secondary side refrigerant passage is formed by said conductive pipe.

23. A charging system for use with an electric vehicle comprising:

a primary coil unit provided in a charging coupler;

a charging power source for exciting said primary coil unit;

a secondary coil unit provided in said electric vehicle which is electromagnetically coupled with said primary coil unit, to thereby generate an electromotive force;

a battery device provided in the electric vehicle which is charged by the electromotive force generated in said secondary coil unit;

wherein a refrigerant of a cooling device provided in said electric vehicle is allowed to flow through said primary coil unit or secondary coil unit to thereby cool the same.

24. A charging system as claimed in claim 23, wherein there is formed in said charging coupler a primary side refrigerant passage through which said refrigerant for cooling said primary coil unit is allowed to flow and, in a receive portion into which said charging coupler can be mounted, there are provided passage joints which can bring said primary side refrigerant passage into communication with the refrigerant passage of said cooling device when said charging coupler is mounted into said receive portion.

25. A charging system as claimed in claim 23, wherein there is formed in said charging coupler a heat transfer member for transferring heat generated in said primary coil unit to the receive portion side into which said coupler can be mounted, and said cooling device cools said heat transfer member to thereby be able to cool said primary coil unit.

26. A charging system as claimed in claim 23, wherein at least one of a primary coil and a secondary coil is formed of a conductive pipe and the refrigerant of said cooling device of said electric vehicle is allowed to flow through the interior portion of said conductive pipe.

* * * * *